United States Patent
Takamatsu et al.

(10) Patent No.: US 8,192,810 B2
(45) Date of Patent: Jun. 5, 2012

(54) METHOD FOR USING STATIC ELECTRICITY REDUCING/REMOVING INSTRUMENT AND STATIC ELECTRICITY REDUCING/REMOVING DEVICE

(76) Inventors: Kuniaki Takamatsu, Yamagata (JP); Nariko Ohara, Nara (JP)

( * ) Notice: Subject to any disclaimer, the term of this patent is extended or adjusted under 35 U.S.C. 154(b) by 186 days.

(21) Appl. No.: 12/623,927

(22) Filed: Nov. 23, 2009

(65) Prior Publication Data

US 2010/0065071 A1 Mar. 18, 2010

Related U.S. Application Data

(62) Division of application No. 09/958,869, filed as application No. PCT/JP01/00570 on Jan. 26, 2001, now Pat. No. 7,638,177.

(30) Foreign Application Priority Data

Feb. 14, 2000 (JP) .................................. 2000-035778
Jun. 16, 2000 (JP) .................................. 2000-182066

(51) Int. Cl.
*B32B 1/02* (2006.01)
*B32B 1/08* (2006.01)
(52) U.S. Cl. ..................... 428/34.4; 428/34.1; 428/34.2; 428/36.9; 428/36.91

(58) Field of Classification Search ................. 428/34.1, 428/34.2, 34.4, 36.9, 36.91
See application file for complete search history.

(56) References Cited

U.S. PATENT DOCUMENTS 4,637,956 A * 1/1987 Das et al. ...................... 428/391

FOREIGN PATENT DOCUMENTS

| EP | 0 806 889 A1 | 11/1997 |
| JP | 09 306692 A | 11/1997 |
| JP | 10233292 | * 9/1998 |

OTHER PUBLICATIONS

Supplemental International Search Report for International Application No. PCT/JP01/00570.

* cited by examiner

*Primary Examiner* — Marc Patterson
(74) *Attorney, Agent, or Firm* — Sorin Royer Cooper LLC

(57) ABSTRACT

A glass container storing unit in which the bottom section of a conical first glass container is stored is supported on one base of a cylindrical motor storing unit in which a motor stored, with a rotation axis. A second glass container in the shape of a Welsh onion flower is attached to the other base of the motor storing unit. Negatively charged metallic silicon is sealed in the first glass container and second glass container. The pointed section of the first glass container is pressed against a human body by rotating the first glass container with the rotation axis.

13 Claims, 17 Drawing Sheets

METHOD FOR USING STATIC ELECTRICITY REDUCING/REMOVING INSTRUMENT AND STATIC ELECTRICITY REDUCING/REMOVING DEVICE

CROSS REFERENCE TO RELATED APPLICATIONS

This application is a divisional application of U.S. patent application Ser. No. 09/958,869, filed on Oct. 12, 2001, entitled "Static Electricity Reducing/Removing Instrument and Static Electricity Reducing/Removing Device."

TECHNICAL FIELD

The present invention relates to static electricity reducing/removing instruments and static electricity reducing/removing devices for relieving muscular pains, such as stiff shoulder and lumbago, and other symptoms.

BACKGROUND ART

Muscular pain is caused by hypertension of muscle and often gives so-called "stiffness" as a subjective symptom. The most typical cause of the stiffness in muscles is fatigue. When muscles have a blood circulation disorder due to fatigue, oxygen and energy source are not sufficiently supplied, and anaerobic glycolysis proceeds actively. As a result, produced fatigue substances such as lactic acid accumulate, proteins in the muscles cause a colloid chemical change, and the hardness of the muscles is increased and gives a state of "stiffness". Moreover, reflex tension of muscles which is produced by such diseases that cause psychentonia and visceral pain is also a cause of the "stiffness" in muscles.

The "stiffness" is recognized as a pain because the sensory nerves distributed in muscles or periosteum to which the muscles attached have a mechanical stimulus by tension of the muscles. A blood flow disorder in muscles causes atrophy of muscle fibers and fat humectation in the muscle fibers, and subsequently occurring circumscribed myositis may cause the "stiffness".

In any case, when the blood flow is decreased by tension of muscles, a micro vasodilator system is activated, and liberation of pain-producing substances such as potassium ions and lactic acid is promoted. Furthermore, in a muscular tissue in which the pH is lowered, the activity of enzymes which destroy the pain-producing substances is limited, and therefore outflow of the pain-producing substances is prevented by ischemia and the pain-producing substances accumulate in muscles and cause pain.

It has been said that the most effective prophylaxis for muscular pain is to strengthen muscles so as to make the muscles less susceptible to fatigue. If a muscular pain occurs, the muscles must rest to remove the fatigue and the blood flow in muscles must be improved by giving a hot compress or massage.

Besides, in the field of oriental medicine, it is an old practice to use methods such as finger-pressing of points (called "effective spots" or "meridian points") on a body surface representing organs in the body, cauterizing the skin with moxa, and acupuncture so as to improve the flow of energy called "natural energy" flowing in meridians (paths connecting the organs in the body and the effective spots) and cure organs that can not be touched directly.

As conventional massage tools for massaging portions having the above-mentioned stiffness and the effective spots, there are a hammer type massage tool for tapping the affected part with its hammer section provided on one end by holding a grip section provided on the other end; a massage tool for pressing the affected part with a pressing section provided on one end by holding a grip section provided on the other end; a pencil type massage tool whose pointed end is placed on the affected part and vibrated by a motor; etc.

However, the above-mentioned massage tools have problems that the blood flow in muscles is not improved sufficiently with these massage tools and symptoms are not sufficiently relieved. Moreover, since such a tool presses the affected part spot by spot, it is necessary to change the press position a plurality of times in order to massage the affected part entirely.

By the way, it has been known that, when the body surface of a human body or the inside of the body is positively charged, body fluids, such as blood and lymph, and natural energy flow badly and biological functions such as a rise of the blood pressure, an increase in blood glucose, vasoconstriction and diuretic inhibition occur, and consequently the activity of cells is decreased, the person is easily excited, symptoms such as uncomfortable feeling, sleeplessness and anorexia appear, and troubles in terms of beauty, health disorders such as muscular pain, and diseases are induced.

As a method of reducing/removing such static electricity, there are a method in which charges are promptly released by increasing the conductivity of a material (for example, a method in which the material is connected to an earth wire whose one end is buried in ground); a method in which the generated charge is neutralized by supplying ions of different polarity by a charge eliminator using isotopes and AC corona discharge; a method in which atmospheric discharge is performed; etc.

Moreover, in order to prevent the occurrence of troubles in terms of beauty, health disorder and diseases by neutralizing the positive static electricity or turning the positive static electricity into negative static electricity, various types of equipment, such as air cleaners having an additional function of generating negative charges, bedclothes (thick bed-quilt and pillows) and clothes have been developed.

In the former methods, however, it is difficult to completely remove static electricity, and a large-scale device is necessary to turn the positive static electricity into negative static electricity.

Further, negative charges are scattered in the atmosphere from the latter equipment and so on, so that the amount of negative charges which directly act on a human body is small and neutralization of static electricity on the human body, i.e., reduction/removal of static electricity, is not sufficient. Hence, there is a problem that such equipment does not perform a sufficient function.

The present invention was made in view of such circumstances, and an object of the first invention of the present application is to provide a static electricity reducing/removing instrument capable of sufficiently improving the blood flow in muscles by comprising, at the end portion thereof, one or a plurality of first glass container having a pointed section and Si, $SiO_x$ ($0<x\leq2$), mineral, Al, P, Ge, Sn, Pb, Ni or Fe in granular or powder form sealed therein so as to press the pointed section of the first glass container against an affected part. As the oxides of Si, there are not only $SiO_2$ or SiO, but also an oxide with x of a decimal point, and the presence of this oxide is revealed in a thesis "Characteristics of SiO-deposited films" written by Koichi Nagami.

An object of the second invention of the present application is to provide a static electricity reducing/removing instrument capable of facilitating the flow of body fluids, etc. and alleviating symptoms such as muscular pain by neutralizing the positive charges on a human body, i.e., by reducing/removing static electricity by directly supplying negative charges to the human body.

Here, charging a human body negatively means the human body is supplied with negative charges and has negative static electricity, and this is also called negative ionization.

An object of the third invention of the present application is to provide a static electricity reducing/removing instrument capable of improving the directivity of negative charge emission by the first glass container having a substantially conical shape.

An object of the fourth invention of the present application is to provide a static electricity reducing/removing instrument capable of highly immediately removing static electricity and removing static electricity in deep part of a human body by comprising a driver for vibrating the first glass container or rotating the first glass container about the center axis of the pointed section.

An object of the fifth invention of the present application is to provide a static electricity reducing/removing instrument capable of enhancing the effect by sealing in the first glass container micro glass containers in which negatively charged Si or the like is sealed.

An object of the sixth invention of the present application is to provide a static electricity reducing/removing instrument capable of realizing a long life of the driver and preventing breakdown of the first glass container and adhesion of iron dioxide as an impurity to the inner wall of the first glass container by comprising, on the other end, a second glass container having a pointed section and negatively charged Si or $SiO_x$ ($0<x\leqq2$) in granular or powder form sealed therein.

Objects of the seventh and eighth invention of the present invention are to provide a static electricity reducing/removing instrument capable of limiting a decrease of negative charges with time by placing Si or the like in a stationary state at a location where static electricity reducing/removing means is buried or introducing Si or the like in a quartz crucible supplied with negative charges and then sintering the Si or the like to fix the negative charges to the Si or the like.

Objects of the ninth and tenth inventions of the present application are to provide a static electricity reducing/removing device capable of fixing a static electricity reducing/removing instrument during rotation, strongly reducing/removing static electricity in front of and behind a human body simultaneously, efficiently supplying negative charges to the human body and thereby having excellent effects of relieving symptoms, by supporting the static electricity reducing/removing instrument with a supporting base.

DISCLOSURE OF THE INVENTION

A static electricity reducing/removing instrument of the first invention is characterized by comprising, at one end portion thereof, one or a plurality of first glass container having a pointed section and Si, $SiO_x$ ($0<x\leqq2$), mineral, Al, P, Ge, Sn, Pb, Ni or Fe in granular or powder form sealed therein.

According to the first invention, by pressing the pointed section of the first glass container against an affected part, the blood flow in muscles can be improved sufficiently, and particularly when a plurality of the first glass containers are included, static electricity can be reduced/removed efficiently.

A static electricity reducing/removing instrument of the second invention is characterized by comprising, at one end portion thereof, one or a plurality of first glass container having a pointed section and negatively charged Si, $SiO_x$ ($0<x\leqq2$), mineral, Al, P, Ge, Sn, Pb, Ni or Fe in granular or powder form sealed therein.

The first glass container in a conical shape with a base having a diameter of 6 cm and a height of 6 cm in which negatively charged Si by a later-described method is sealed is placed in a Faraday cage available from Shimadzu Corporation, and the amount of charge was measured by the stick monitor M6 available from Shimadzu Corporation. As a result, it was known that the amount of charge in the Faraday cage was $-1.075\times10^{-9}$ coulomb and the number of ions was approximately 67 hundred million, and thus it was confirmed that the glass container was negatively charged.

According to the second invention, the first glass container in which negatively charged Si or the like is sealed is included, and negative charges are emitted from the pointed section of this first glass container. It has been known that, when the negative charges are supplied to a living body and then positive static electricity on an affected part is reduced/removed, the flow of body fluids is facilitated, and biological functions such as a lowering of the blood pressure, a decrease in blood glucose, vasodilation and promotion of diuresis are performed; and, when this static electricity reducing/removing instrument is used, negative charges are efficiently supplied to a human body and the static electricity on the human body is reduced/removed, thereby alleviating symptoms such as muscular pain.

A static electricity reducing/removing instrument of the third invention is based on the first or second invention, and characterized in that the first glass container has a substantially conical shape.

According to the third invention, since the glass container has a substantially conical shape, the directivity of negative charge emission is improved.

A static electricity reducing/removing instrument of the fourth invention is based on the first or second invention, and characterized by comprising a driver for vibrating the first glass container or rotating the first glass container about the center axis.

The electrostatic potentials in the vicinity of the glass container were measured for each of the cases where the first glass container was in a stationary, vibrated or rotated state. The measurement conditions are as follows.

Measuring room: 6 m×9 m×2.7 m
Room temperature: 24° C.
Humidity: 33%
Measuring device: Electrostatic potential measuring device (KSD0103 available from Kasuga Electric Works Ltd.)
First glass container: 6 cm in the diameter of the base, 6 cm in height, later-described sintered metallic silicon being sealed.
Measuring method: The electrostatic potential was repeatedly measured a plurality of times by the above-mentioned measuring device, at positions 3 cm apart from the pointed end and base of the first glass container for the three cases:

(1) The first glass container 11 was placed in a stationary state on a table made of an insulator;

(2) The first glass container was placed on a vibrator (S-550 available from Ryobi Ltd.) disposed on the table, and vibrated;

(3) The first glass container was rotated (at a rotation speed of 3200 rpm) by a motor (41K60A-BF available from Oriental Motor Co. Ltd.) disposed on the table.

The results are shown in Table 1.

TABLE 1

|  | Electrostatic potential at the pointed end | | | | | Electrostatic potential at the base | | | | |
| --- | --- | --- | --- | --- | --- | --- | --- | --- | --- | --- |
|  | 1 | 2 | 3 | 4 | 5 | 1 | 2 | 3 | 4 | 5 |
| (1) Stationary | −0.4 | −0.4 | −0.3 | −0.2 | −0.2 | −0.2 | −0.1 | −0.2 | −0.2 | −0.1 |
| (2) Vibrated | −0.7 | −0.8 | −0.9 | −0.9 | −1.0 | −0.3 | −0.3 | −0.3 | −0.5 | −0.4 |
| (3) Rotated | −0.6 | −0.6 | −0.5 | −1.5 | −1.3 | −0.4 | −0.3 | −0.2 | −0.3 | −0.2 |
|  | −1.8 | −1.0 | −2.0 | −1.6 | −1.4 |  |  |  |  |  |

(unit: kV)

The electrostatic potentials in the room measured in the cases (1), (2) and (3) were −0.1 kV, −0.0 kV, and −0.0 kV, respectively. Note that the electrostatic potential in the room before placing the first glass container was between 0.1 kV and 0.2 kV. It was confirmed from Table 1 that the first glass container emitted negative charges and the absolute value of the potential was highest in (3) of the rotated case, and the absolute value decreased in the order of (2) of the vibrated case and (1) of the stationary case.

According to the fourth invention, since the driver for rotating or vibrating the glass container is included and the glass container is rotated or vibrated during application, as described above, a larger amount of negative charges are emitted, the immediate effect of removing static electricity from a human body becomes higher, and static electricity in deep part can be removed. Accordingly, when this electrostatic reducing/removing tool comes into contact with the affected part of the human body, the flow of body fluids is further facilitated, thereby alleviating the symptoms.

A static electricity reducing/removing instrument of the fifth invention is based on the second invention, and characterized in that the first glass container comprises a plurality of micro glass containers in which negatively charged Si, $SiO_x$ ($0<x\leq2$), mineral, Al, P, Ge, Sn, Pb, Ni or Fe in granular or powder form is sealed.

Metallic silicon and 1000 conical first glass containers having a base with a diameter of 3 mm and a height of 3 mm are sealed in a conical first glass container having a base with a diameter of 18 cm and a height of 18 cm, and the electrostatic potential of the glass of the first glass container was measured by the above-mentioned electrostatic potential measuring device (at room temperature of 20° C. and humidity of 60%). The result was 0.0 V. The electrostatic potential was also 0.0 V when the first glass container was rotated. In this case, the electrostatic potentials in the room space was 0.2 kV before the first glass container 1 was rotated, −0.2 kV immediately after starting rotation, and −0.0 kV after 1 to 5 minutes from the rotation.

A static electricity reducing/removing instrument comprising the first glass container in which metallic silicon is sealed and a static electricity reducing/removing instrument of the fifth invention comprising the first glass container in which the micro glass containers are sealed in addition to the metallic silicon were brought into contact with human bodies while rotating their first glass container. It was confirmed that blisters were formed on the skin when the former static electricity reducing/removing instrument was used, but blisters were not formed or the degree of blisters was lessened when the latter static electricity reducing/removing instrument was used.

A static electricity reducing/removing instrument of the sixth invention is based on the second invention, and characterized by further comprising, at the other end portion thereof, a second glass container having a pointed section and negatively charged Si or $SiO_x$ ($0<x\leq2$) in granular or powder form sealed therein.

According to the sixth invention, since the second glass container having a pointed section and negatively charged Si or $SiO_x$ sealed therein is provided on the other end, it is possible to shorten the press time to human body and realize a long life of the driver; and it is also confirmed through experiments that the sixth invention can prevent breakdown of the first glass container and adhesion of iron dioxide as an impurity to the inner wall of the first glass container.

A static electricity reducing/removing instrument of the seventh invention is based on the second invention, and characterized in that the negatively charged Si, $SiO_x$ ($0<x\leq2$), mineral, Al, P, Ge, Sn, Pb, Ni or Fe in granular or powder form was produced through a first process of placing the granules or powder in a stationary state at a location where static electricity reducing/removing means formed by sealing negatively charged Si or $SiO_x$ ($0<x\leq2$) in granular or powder form in a glass tube is buried in ground; and a second process of sintering the Si, $SiO_x$ ($0<x\leq2$), mineral, Al, P, Ge, Sn, Pb, Ni or Fe treated by the first process, for a predetermined time.

A static electricity reducing/removing instrument of the eighth invention is based on the second invention, and characterized in that the negatively charged Si, $SiO_x$ ($0<x\leq2$), mineral, Al, P, Ge, Sn, Pb, Ni or Fe in granular or powder form was produced through a first process of introducing the granules or powder in a negatively charged quartz crucible; and a second process of sintering the Si, $SiO_x$ ($0<x\leq2$), mineral, Al, P, Ge, Sn, Pb, Ni or Fe treated by the first process, for a predetermined time at a location where static electricity reducing/removing means formed by sealing negatively charged Si or $SiO_x$ ($0<x\leq2$) in granular or powder form in a glass tube is buried in ground.

According to the seventh and eighth inventions, since Si or the like is placed in a stationary state at a location where the static electricity reducing/removing means is buried, or Si or the like is introduced into the negatively charged quartz crucible, negative charges migrate to the Si or the like, and the Si or the like turns into a negatively charged state. In the following second process, by sintering the Si or the like at the location where the static electricity reducing/removing means is buried, the negative charges are fixed to the Si or the like, thereby limiting a decrease of negative charges with time. When a static electricity reducing/removing instrument is constructed by sealing Si or the like negatively charged in this manner in the first glass container, negative charges are efficiently supplied during application, thereby reducing/removing the static electricity on a human body.

A static electricity reducing/removing device of the ninth invention is characterized by comprising one or a plurality of supporting base for freely elevating and lowering one or a plurality of the static electricity reducing/removing instrument of the first or second invention in a state in which the static electricity reducing/removing instrument faces a human body.

A static electricity reducing/removing device of the tenth invention is characterized by comprising one or a plurality of supporting base for supporting one or a plurality of the static electricity reducing/removing instrument of claim 1 or 2 so that the static electricity reducing/removing instrument is movable forward and backward along a direction approaching a human body.

According to the ninth and tenth invention, the static electricity reducing/removing instrument which is heavy in weight is supported on the supporting base, and the pointed end of the first glass container can be brought into contact with an affected part accurately by fixing the static electricity reducing/removing instrument during rotation. Moreover, since reduction/removal of static electricity can be performed for the front and back sides of a human body simultaneously, negative charges are efficiently supplied to the human body, thereby enhancing the effects of relieving symptoms.

BEST MODE FOR CARRYING OUT THE INVENTION

The following description will explain the present invention with reference to the drawings illustrating some embodiments thereof.

First Embodiment

Figure 1:
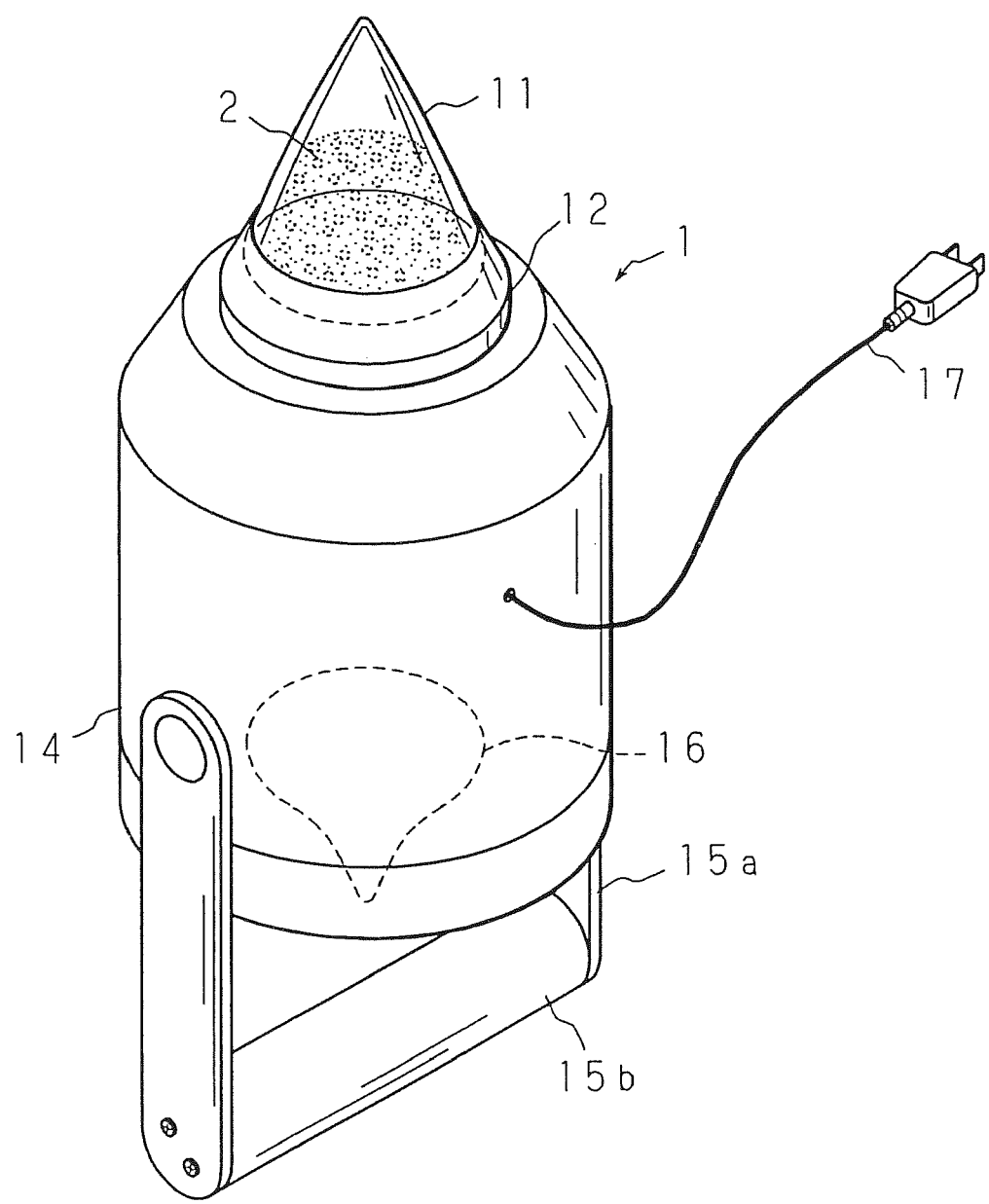
FIG. 1 is a perspective view showing a static electricity reducing/removing instrument according to the first embodiment of the present invention.
Figure 2:
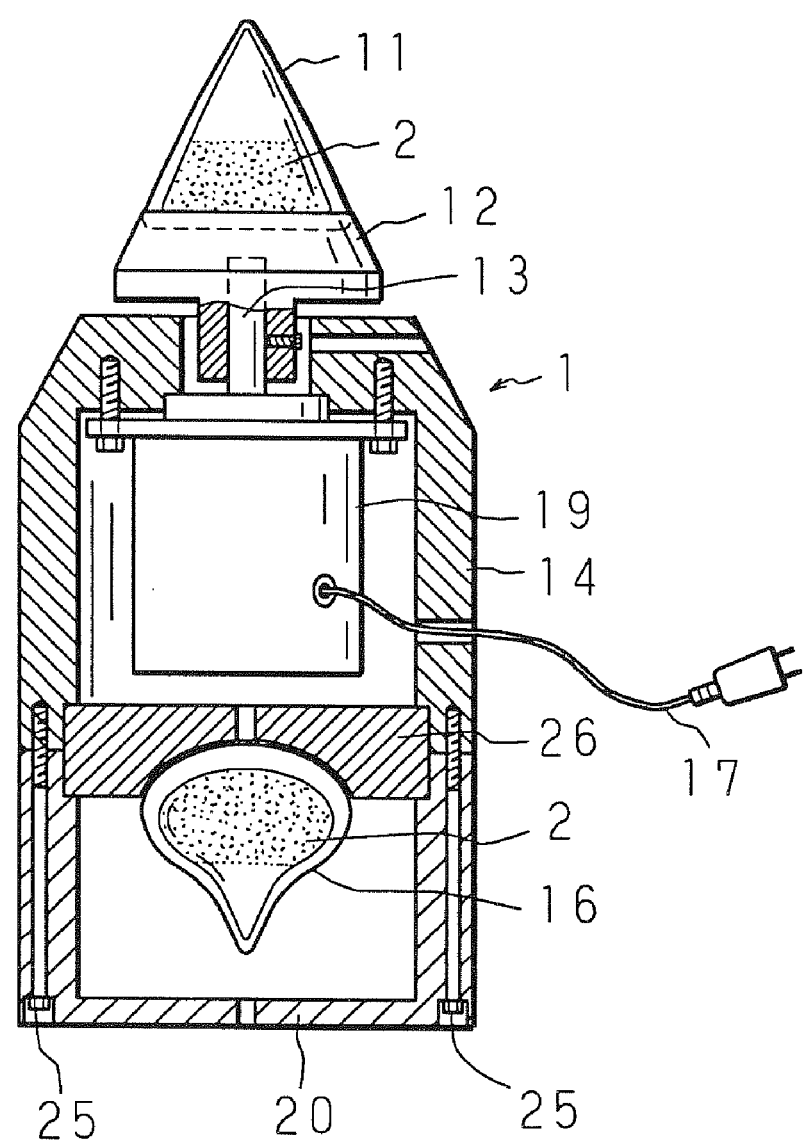
FIG. 2 is a cross sectional view showing the static electricity reducing/removing instrument according to the first embodiment of the present invention.

FIG. 1 is a perspective view showing a static electricity reducing/removing instrument according to the first embodiment, and FIG. 2 is a cross sectional view thereof, wherein 1 is the static electricity reducing/removing instrument.

The static electricity reducing/removing instrument 1 has a cylindrical motor storing unit 14 in which a motor 19 (41K60A-BF available from Oriental Motor Co. Ltd.: 60 W output, 1.85 kg/cm rating torque, 3200 rpm rated speed) is fastened with screws. One end of the motor storing unit 14 is formed in a tapered shape, and a glass container storing unit 12 in which the bottom section of a conical first glass container 11 is stored is supported on this one end by a rotation axis 13 attached to the motor 19.

A bottom rid section 20 is attached to the other end of the motor storing unit 14 with bolts 25. A disk-shaped second glass container attachment plate 26 is provided between the motor 19 and the bottom rid section 20 so as to be parallel with them, and a second glass container 16 in the shape of a Welsh onion flower is attached to the lower face of the second glass container attachment plate 26 so that its pointed section faces the bottom rid section 20. Each of the first glass container 11 and second glass container 16 has a base with a diameter of 60 mm and a height of 60 mm, and granular metallic silicon 2 which has been negatively charged by a later-descried method is sealed therein.

A handle 15 constructed by arm sections 15a and a grip section 15b bridging the ends of the respective arm sections 15 is attached to substantially the middle of the motor storing unit 14 so that the handle 15 can be turned freely, and a power supply code 17 is connected to the motor 19.

The static electricity reducing/removing instrument 1 of this first embodiment is 330 mm in the entire length including the first glass container 11, 150 mm in diameter, and 7.5 kg in weight.

The metallic silicon sealed in the first glass container 11 and second glass container 16 is supplied with negative charges in the following manner.

Figure 3:
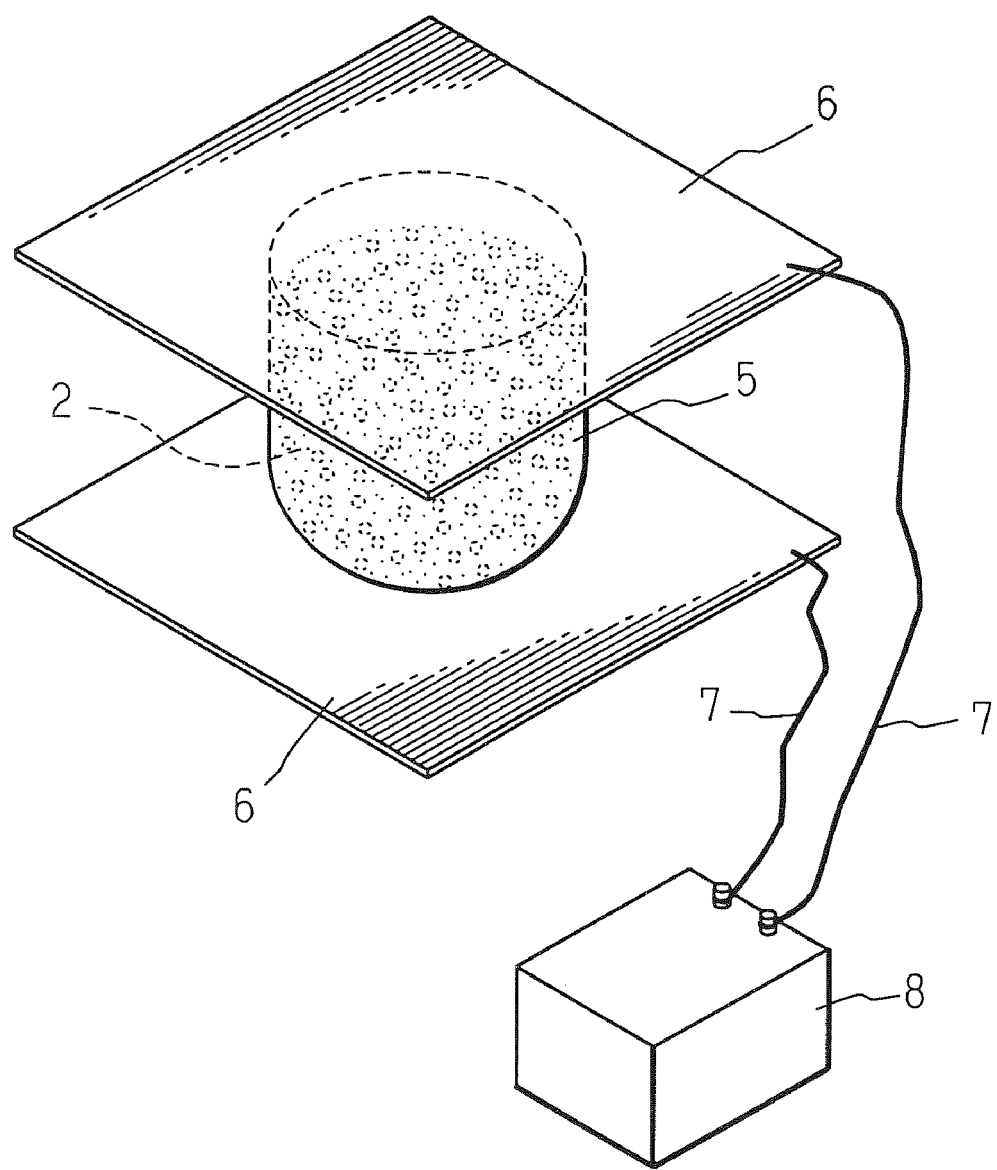
FIG. 3 is a perspective view showing a negative charge supply device applied to the manufacture of static electricity reducing/removing instruments according to the present invention.

FIG. 3 is a perspective view showing a negative charge supply device which is employed for the manufacture of static electricity reducing/removing instruments according to the present invention.

The negative charge supply device includes a quartz crucible 5, copper plates 6, codes 7, and a static electricity reducing/removing device 8. The static electricity reducing/removing device 8 is disclosed in Japanese Laid-Open Patent Publication No. 11-87086/1999. The open-side outer edge section and the bottom section of the quartz crucible 5 having an open face with an inner diameter of substantially 40 cm and a height of substantially 40 cm are respectively connected to the static electricity reducing/removing device 8 through the copper plate 6 and the code 7.

The static electricity reducing/removing device 8 is activated to supply negative charges to the quartz crucible 5 for around 3 hours, and, after sufficiently removing positive static electricity from the quartz crucible 5, 1 kg of metallic silicon (a particle diameter of 0.2 to 2 mm: available from Elkem) 2 with Si purity of 99.5% is introduced into the quartz crucible 5 from the opening side and left for a predetermined time (3 to 15 minutes) in a state in which the static electricity reducing/removing device 8 is being activated so as to negatively charge the metallic silicon 2.

Next, the metallic silicon 2 is sintered.

Figure 4:
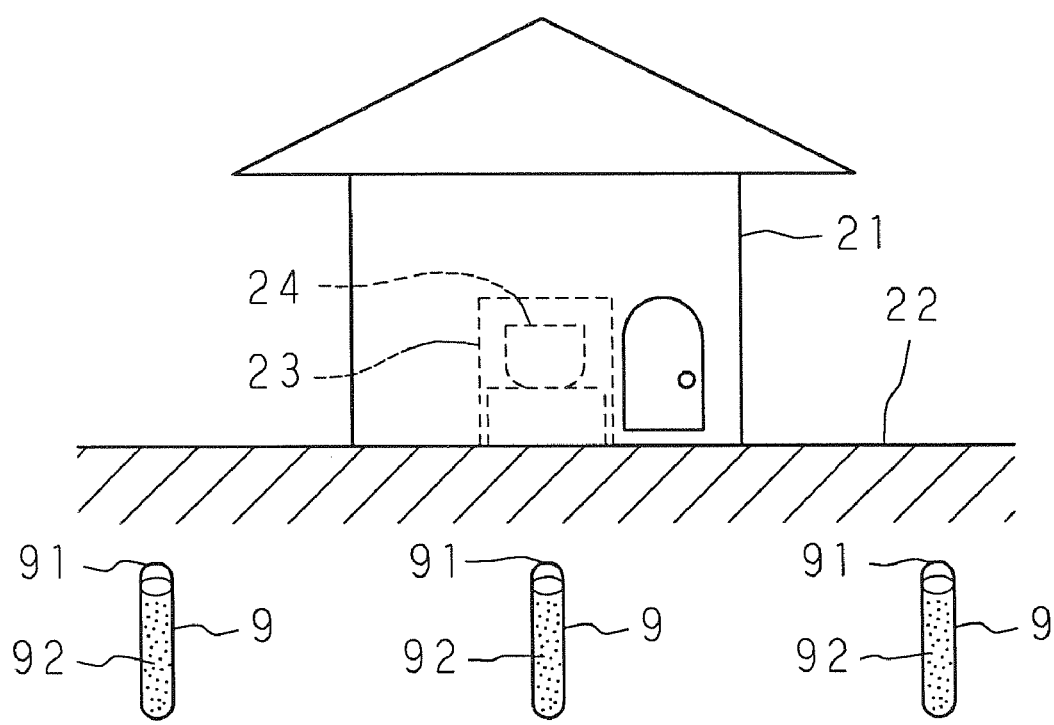
FIG. 4 is a side view showing a building and site for sintering metallic silicon.
Figure 5:
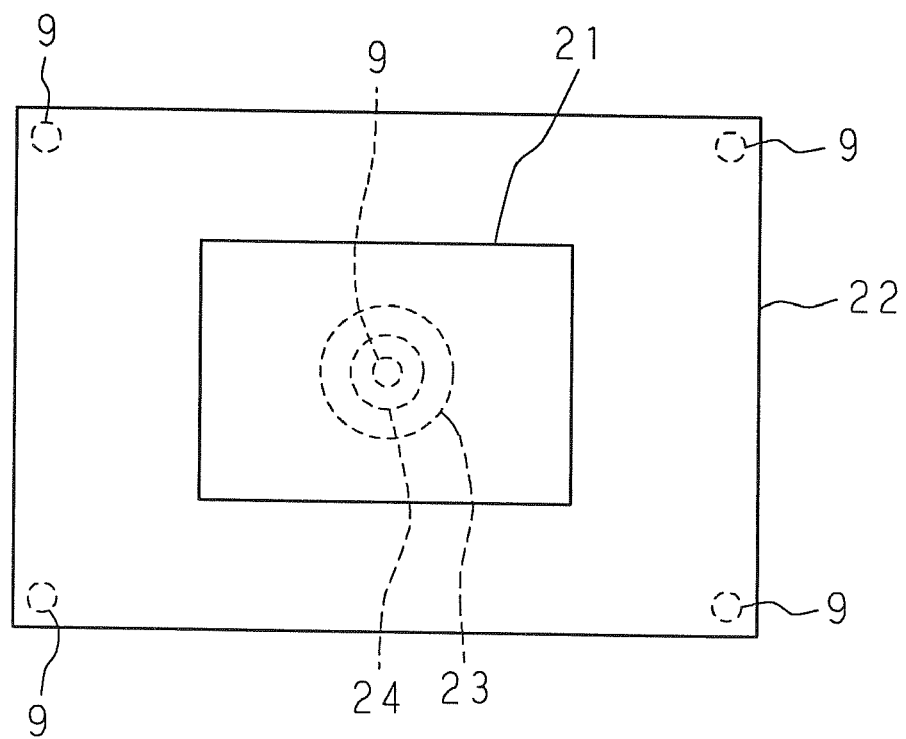
FIG. 5 is a plan view showing the building and site for sintering metallic silicon.

FIG. 4 is a side view showing a building and site for sintering the metallic silicon 2, and FIG. 5 is a plan view thereof. A building 21 (3.6 m×9.0 m base) is built at the center of a site 22 of 100 tsubo (about 330 square meters). An ion bar 9 (Japanese Patent No, 2896762) produced by sealing 5 to 6 kg of silicon (Si) 92 in granular or powder form in a glass tube 91 of a length of 1.5 m and a diameter of 8 cm and tightly closing the glass tube 91 is buried under ground at a depth of 5 m, at the four corners and center of the site 22 (the center of the building 21) so that a longitudinal direction of the ion bars 5 coincides with a vertical direction. An electric furnace 23 is disposed at the center of the building 21.

The metallic silicon 2 which has been negatively charged in the above-mentioned manner is moved from the quarts crucible 5 to a ceramic crucible 24, and then placed in the electric furnace 23 and sintered at 800 to 1300° C. for 30 minutes to 2 hours. The crucible 24 has a base with a diameter of 30 cm and a height of 20 cm. Like the quartz crucible 5, this crucible 24 has been supplied with negative charges beforehand. After sintering, the metallic silicon 2 has any one of colors, red, blue, green, yellow, purple and dark red.

Note that the length and diameter of the glass tube 91 of the ion bar 9 and the amount of Si 92 can be selected suitably according to the sizes of the building 21 and site 22, and other factor. The buried position and depth of the ion bars 9 and the number of ion bars 9 are also selected suitably by considering the sizes and shapes of the building 21 and site 22, and other factor.

Besides, in this embodiment, while the Si 92 is sealed in the glass tube 91, $SiO_x$ may be sealed. In this case, $x$ preferably satisfies $1.0 < x \leq 2.0$.

Furthermore, instead of using the negative charge supply device shown in FIG. 3, it is possible to leave the metallic silicon 2 in the site 22 for 1 day to 1 week or more and then sinter the metallic silicon 2.

5 kg of the sintered metallic silicon 2 was put into a vinyl bag and moved into a paper box (30 cm×30 cm×10 cm) from a position at a height of 20 cm so as to measure the electrostatic potential on the paper box with the above-mentioned electrostatic potential measuring device, and the results are shown in Table 2 below.

TABLE 2

|  | First time | Second time | Third time | Fourth time | Fifth time |
|---|---|---|---|---|---|
| Just after moved | −13.5 | −12.0 | −13.0 | −12.5 | −14.0 |
| 1 min. later | −5.0 | −5.5 | −5.8 | −5.6 | −5.0 |
| 2 min. later | −2.3 | −2.2 | −2.3 | −2.1 | −2.0 |
| 3 min. later | −1.9 | −2.0 | −2.1 | −1.9 | −1.9 |
| 5 min. later | −1.4 | −1.4 | −1.4 | −1.4 | −1.4 |
| 10 min. later | −1.2 | −1.1 | −1.1 | −1.1 | −1.2 |

(unit: kV)

It will be understood from Table 2 that the metallic silicon 2 is negatively charged.

Next, the conical first glass container having a base with a diameter of 18 cm and a height of 18 cm in which 1.2 kg of the sintered metallic silicon was sealed was placed on an insulator, and the electrostatic potential at a position diagonally above this first glass container was measured 15 times by the above-mentioned electrostatic potential measuring device. The results were −0.0, −0.1, −0.3, −0.2, −0.1, −0.1, −0.0, −0.0, −0.2, −0.2, −0.2, −0.0, −0.3, −0.0, −0.1, −0.0, −0.0, and −0.3 kV, respectively.

The static electricity reducing/removing instrument 1 according to the present invention may be used in such a manner that it is pressed against a human body with the first glass container 11 in a stationary state or in a vibrated or rotated state. When the static electricity reducing/removing instrument 1 is used with the first glass container 11 being in a stationary state, the static electricity on the human body is gradually removed; whereas when the static electricity reducing/removing instrument 1 is used with the first glass container 11 being rotated, it can remove the static electricity quickly and has a highly immediate effect. Moreover, it is also possible to remove the static electricity in deep part of the human body.

In order to examine the effect of vibrating or rotating the first glass container 11, the hair was stroked with the first glass container 11, and the electrostatic potentials of the hair before and after stroking were measured. The measurement conditions are as follows.

Measuring room: 6 m×9 m×2.7 m
Room temperature: 24° C.
Humidity: 33%
Measuring device: Electrostatic potential measuring device (KSD0103 available from Kasuga Electric Works Ltd.)
First glass container 11: 6 cm in diameter of the base, 6 cm in height, metallic silicon 2 being sealed.
Measuring method: The hair was entirely stroked with the vertex of the first glass container 11 for 30 seconds for the three cases:
 (1) The first glass container 11 was in a stationary state;
 (2) The first glass container 11 was placed on a vibrator (S-550 available from Ryobi Ltd.) and vibrated;
 (3) The first glass container 11 was rotated (at a rotation speed of 2900 rpm) by a motor (41K60A-BF available from Oriental Motor Co. Ltd.), and measurement of the electrostatic potentials of the hair before and after stroking were repeated a plurality of times. The results are shown in Table 3.

TABLE 3

|  | Before Stroking | | | | | After stroking | | | | |
|---|---|---|---|---|---|---|---|---|---|---|
|  | 1 | 2 | 3 | 4 | 5 | 1 | 2 | 3 | 4 | 5 |
| (1) Stationary | 7.3 | 10.8 | 6.8 | 7.5 | 5.3 | 1.6 | 1.8 | 1.7 | 1.2 | 1.2 |
| (2) Vibrated | 0.4 | 1.9 | 0.5 | 0.6 | 0.7 | −0.5 | −0.6 | −0.6 | 0.0 | −0.3 |
| (3) Rotated | 17.4 | 14.3 | 12.4 | 16.4 | 14.4 | −0.3 | 0.0 | 0.0 | 0.0 | 0.0 |

(unit: kV)

It was confirmed from Table 3 that the positive static electricity on the human body would become substantially zero and be further turned into negative static electricity by bringing the first glass container 11 into contact with the human body. Furthermore, it was confirmed that the effect would be highest in (3) of the rotated case, and the greatness of the effect would decrease in the order of (2) of the vibrated case and (1) of the stationary case.

Besides, in the case where the second glass container 16 was not mounted on the base of the motor storing unit 14, iron dioxide adhered to the inner wall of the first glass container 11 and the wall face turned into brown after using the static electricity reducing/removing instrument 1, but it was confirmed that this problem would be solved, the immediate effect of removing and removing static electricity would be enhanced and the static electricity removing effect would continue by mounting the second glass container 16.

In the event when the static electricity reducing/removing instrument 1 is pressed against a human body while rotating the first glass container 11 by the rotation axis 13, a towel folded 8 times is placed on an affected part and a plurality of positions of the towel is pressed by the pointed section. When a portion of the affected part where the amount of charge is large is pressed, the towel would be burnt black in 1 to 10 seconds. When such a portion is pressed for 20 to 30 seconds or more, the towel would be torn, and the pointed end of the first glass container 11 would come into contact with the skin and the skin would be burnt.

It will be understood that the cause of burning of the towel is static electricity, from the facts that the towel was burnt black in 1 to 3 seconds when the towel folded eight times was placed on an electric carpet with an electrostatic potential of 5 to 20 kV (measured by the electrostatic potential measuring device KSD0103 available from Kasuga Electric Works Ltd.) and pressed by the first glass container 11 being rotated, whereas the towel was not burnt black when the towel was placed on a place such as on a desk which was not charged by static electricity and pressed for 5 to 10 seconds by the first glass container 11 being rotated in the same manner as above.

Next, the following description will explain specific cases where the static electricity reducing/removing instrument 1 according to the first embodiment was used for human bodies, and the effects of using the static electricity reducing/removing instrument 1. The first glass container 11 was rotated at a rotation speed of 3200 rpm during application.

(Case 1)

A male in his thirties had symptoms of lumbago and stiff shoulders, but the pain was removed and he became able to bend forward easily after using the static electricity reducing/removing instrument 1.

(Case 2)

A female in her forties had symptoms of stiff shoulders and muscular pain in her whole body, but the muscles in the whole body were softened and she became nimble after using the static electricity reducing/removing instrument 1.

(Case 3)

A female in her thirties had symptoms of listlessness in her whole body, but she felt lighter in the whole body after using the static electricity reducing/removing instrument 1.

(Case 4)

A male in his forties had a slight pain in his neck, but the pain in the neck was alleviated and he felt lighter in his whole body after using the static electricity reducing/removing instrument 1.

(Case 5)

A male in his seventies had stiff shoulders and was in pain and torment for tens of years, but the stiff shoulders disappeared, the pain was removed and the whole body became nimble after using the static electricity reducing/removing instrument 1.

(Case 6)

A male in his twenties had symptoms of a sick feeling in the stomach and chronic diarrhea, but the sick feeling in the stomach was alleviated by half and the number of times of diarrhea was also reduced by half after using the static electricity reducing/removing instrument 1.

(Case 7)

A male in his fifties had a symptoms of lacking vitality and lacking strength in his whole body, but the whole body was energized by the use of the static electricity reducing/removing instrument 1.

(Case 8)

A female in her fifties had symptoms of pain in her left scapula and lumbago, but the pain was alleviated by the use of the static electricity reducing/removing instrument 1.

(Case 9)

A female in her thirties had symptoms of having a stiffness in her shoulder and a low scratching sound when she turned her neck, but the stiffness in the shoulder disappeared and the low scratching sound in the neck was alleviated after using the static electricity reducing/removing instrument 1.

(Case 10)

A male in his fifties had symptoms of stiff and painful shoulders and pain in his stomach, but the stiffness in the shoulders and tension in the nape disappeared and the pain he used to feel about two hours later after eating disappeared by the use of the static electricity reducing/removing instrument 1.

The progress was examined for the male of Case 5 and the female of Case 8. In the case of the male of Case 5, while the effects of conventional treatments continued for only around 3 days to 1 week, he did not have pain in his shoulders even after 26 days from the treatment using the static electricity reducing/removing instrument 1. In the case of the female of Case 8, she had almost no pain in her arms until 8 days after the treatment.

For the male of Case 5, the first glass container 11 was pressed against the affected part for 10 seconds; but the first glass container 11 was pressed against the female of Case 8 for only 2 to 3 seconds because she felt pain. It is therefore considered that, when the first glass container 11 is pressed against the mostly charged portion of the affected part for a certain period of time or more, the static electricity on the affected part is removed sufficiently and a state in which the symptoms are alleviated will continue.

In the case where the first glass container 11 is used while being rotated, if the range of the affected part is narrow as in the case of stiff and painful shoulders, it is possible to remove the pain by pressing a plurality of positions in the affected part for 5 to 10 minutes (by pressing 100 to 200 times). If the range of the affected part is wide as in the case of lumbago, it is considered that it is necessary to apply the 5- to 10-minute treatment 3 to 10 times per day because the pain would not be removed by one treatment.

Second Embodiment

Figure 6:
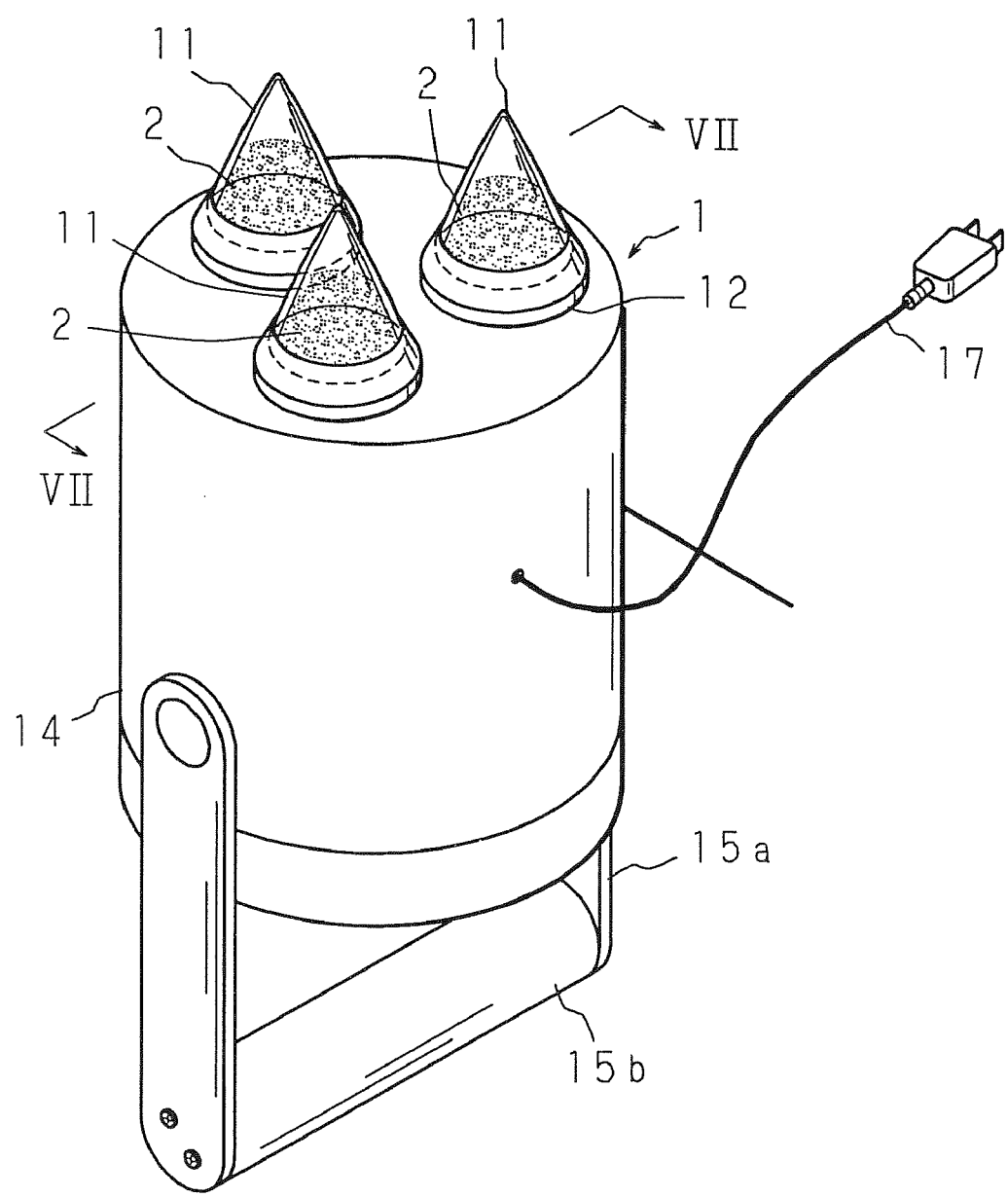
FIG. 6 is a perspective view showing a static electricity reducing/removing instrument according to the second embodiment of the present invention.
Figure 7:
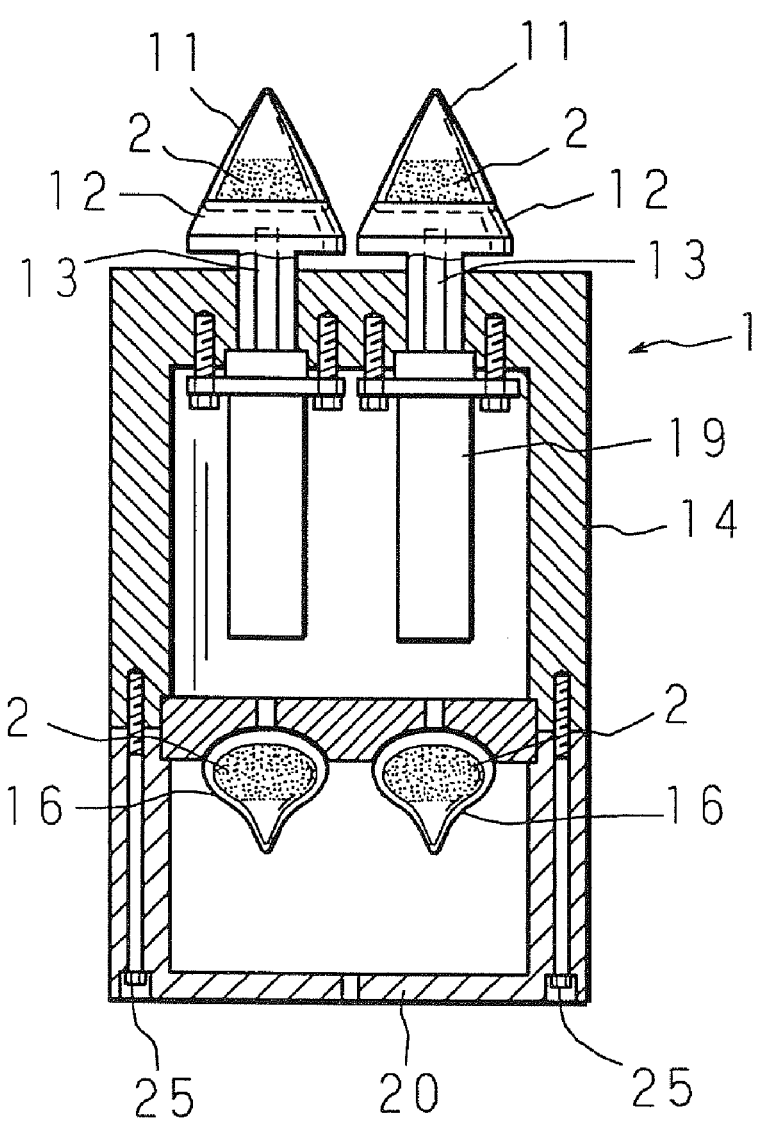
FIG. 7 is a cross sectional view showing the static electricity reducing/removing instrument according to the second embodiment of the present invention.

FIG. 6 is a perspective view showing a static electricity reducing/removing instrument according to the second embodiment, and FIG. 7 is a cross sectional view thereof cut along the VII-VII line. In FIGS. 6 and 7, the same parts as those shown in FIGS. 1 and 2 are designated with the same codes.

The motor storing unit 14 has a diameter of 135 mm and a height of 130 mm; and the first glass container 11 has a base with a diameter of 30 mm and a height of 30 mm. This static electricity reducing/removing instrument 1 has three first glass containers 11 and three second glass containers 16. The second glass containers 16 are mounted in the motor storing unit 14 in such a manner that their pointed sections face the bottom rid 20. The three first glass containers 11 are mounted on the base of the motor storing unit 14 so that the distance between the pointed sections of the respective first glass containers 11 is substantially 50 mm.

In this static electricity reducing/removing instrument 1, since three first glass containers 11 and three second glass containers 12 are included, it is possible to reduce/remove static electricity more efficiently, find an affected part such as a part having severe "stiffness" more quickly and relieve the symptom rapidly as compared with a tool comprising only one first glass container 11 and one second glass container 16.

Next, the following description will explain specific cases in which the static electricity reducing/removing instrument 1 according to this second embodiment was used for human bodies, and the effects of using the static electricity reducing/removing instrument 1. The first glass containers 11 were rotated at a rotation speed of 3000 rpm during application. One 5- to 10-minute treatment was applied to each person. The period of one pressing is 3 to 30 seconds, and pressing was performed while changing the press position along the cells of muscles. The strength of pressing was 0 to 1 kg more than the 3.5 kg self-weight of the static electricity reducing/removing instrument 1, and the static electricity reducing/removing instrument 1 was pressed against the affected part over a bath towel folded four times.

(Case 1)

A male in his fifties was slightly strained and had a symptom of systemic languor, but the systemic languor disappeared by the use of the static electricity reducing/removing instrument 1 of the second embodiment for his back, and he obtained refreshed feeling that he could never had by using other static electricity reducing/removing instruments, (Case 2)

A female in her sixties had a symptom of constipation, but the constipation was solved immediately after the use of the static electricity reducing/removing instrument 1 because the tool 1 effectively acted on the effective spots.

(Case 3)

A female in her thirties was slightly strained, but her whole body was relaxed by the use of the static electricity reducing/removing instrument 1, and the strain in her eyes was removed and she could see clearly after the use of the tool 1.

(Case 4)

A male in his forties had a pain in his left knee, but the pain was alleviated by the use of the static electricity reducing/removing instrument 1 on the back of the left knee. Moreover, he had a symptom of lumbago, the symptom was alleviated by reducing/removing the static electricity on his right lumbar and back. Further, by reducing/removing the static electricity on an area ranging from the neck to the head and around the ears, he felt light in the head and his vision became clear.

(Case 5)

A female in her thirties had symptoms of stiff shoulders and tiredness, but the symptoms were alleviated by the use of the static electricity reducing/removing instrument 1, and the symptoms did not rebound.

(Case 6)

A female in her seventies had difficulty in raising her right arm and frequently receive acupressure treatments, but she could more easily raise the arm after using the static electricity reducing/removing instrument 1 than having the acupressure treatment.

(Case 7)

A female in her thirties had symptoms of feeling heavy in the head and difficult breathing, but she did not feel heavy in the head and could easily breath after reducing/removing static electricity by the static electricity reducing/removing instrument 1.

Third Embodiment

Figure 8:
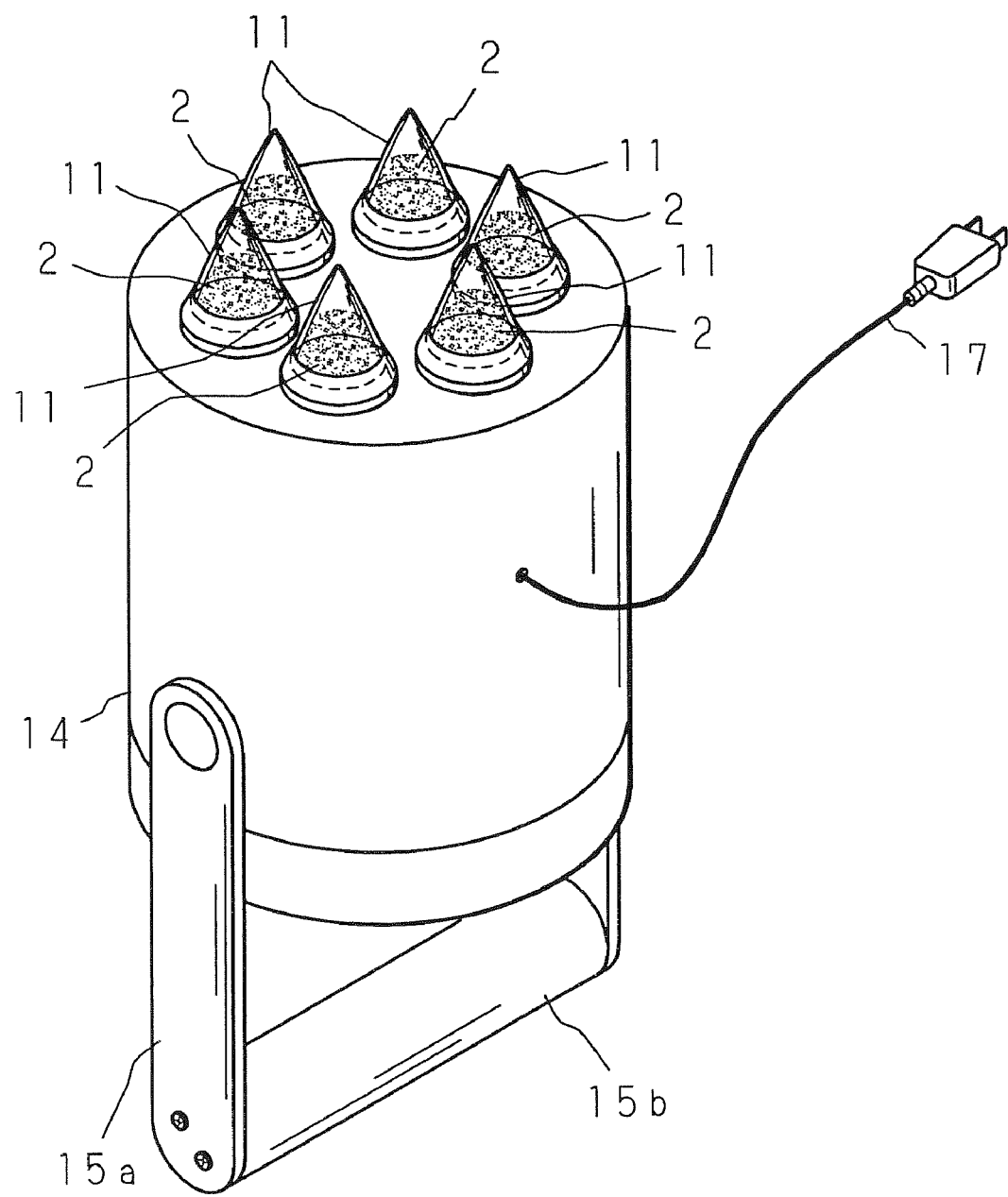
FIG. 8 is a perspective view showing a static electricity reducing/removing instrument according to the third embodiment of the present invention.

FIG. 8 is a perspective view showing a static electricity reducing/removing instrument according to the third embodiment. In FIG. 8, the same parts as those shown in FIGS. 1 and 2 are designated with the same codes.

The motor storing unit 14 has a diameter of 300 mm and a height of 130 mm; and the first glass container 11 has a base with a diameter of 30 mm and a height of 30 mm. The total weight of this static electricity reducing/removing instrument 1 is substantially 9.0 kg.

This static electricity reducing/removing instrument 1 has six first glass containers 11 and six second glass containers 16. The second glass containers 16 are mounted in the motor storing unit 14 in such a manner that their pointed sections face the bottom rid 20. The six first glass containers 11 are mounted on the base of the motor storing unit 14. The internal structure of this static electricity reducing/removing instrument 1 is the same as the static electricity reducing/removing instrument 1 of the second embodiment shown in FIG. 7.

In this static electricity reducing/removing instrument 1, since six first glass containers 11 and six second glass containers 12 are provided, it is possible to more efficiently reduce/remove static electricity, more quickly find an affected part such as a part having severe "stiffness" and rapidly improve the symptom as compared with the tool of the second embodiment comprising three first glass containers 11 and three second glass containers 16. It was possible to reduce the press time of the static electricity reducing/removing instrument 1 of this third embodiment to substantially one second of the press time of the static electricity reducing/removing instrument 1 of the second embodiment comprising three first glass containers 11.

Fourth Embodiment

Figure 9:
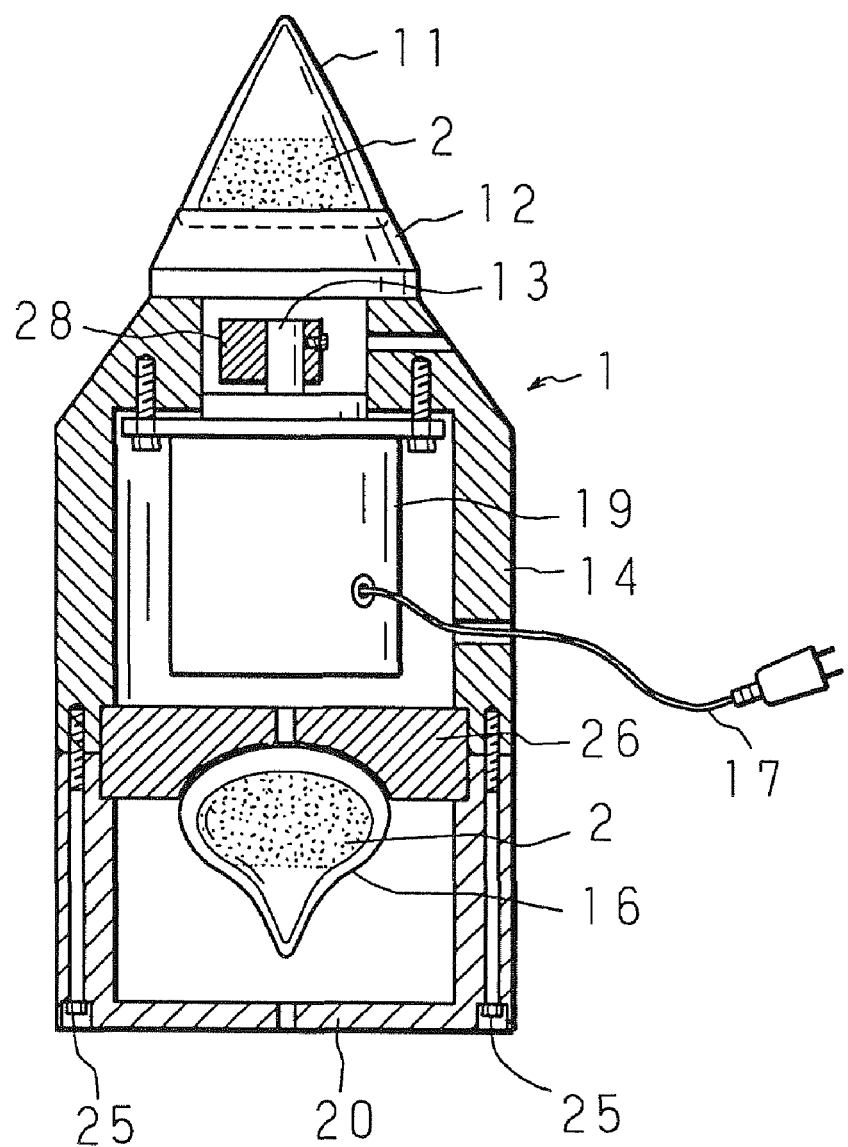
FIG. 9 is a cross sectional view showing a static electricity reducing/removing instrument according to the fourth embodiment of the present invention.

FIG. 9 is a cross sectional view showing a static electricity reducing/removing instrument according to the fourth embodiment, in which the same parts as those shown in FIGS. 1 and 2 are designated with the same codes.

In this static electricity reducing/removing instrument 1, the second glass container 16 is fixed to the motor storing unit 14, and an eccentric weight 28 is attached to the rotation axis 13. The first glass container 11 has a base with a diameter of 60 mm and a height of 60 mm, and the static electricity reducing/removing instrument 1 is 370 mm in the entire length including this first glass container 11, 150 mm in diameter and 8.0 kg in weight.

In this static electricity reducing/removing instrument 1, the eccentric weight 28 is vibrated with rotation of the motor 19, thereby vibrating the first glass container 11.

It has been confirmed that symptoms of stiff shoulders, lumbago, etc. were alleviated by pressing this static electricity reducing/removing instrument 1 against the affected parts of stiff shoulders, lumbago, etc. and vibrating the first glass container 11.

Fifth Embodiment

Figure 10:
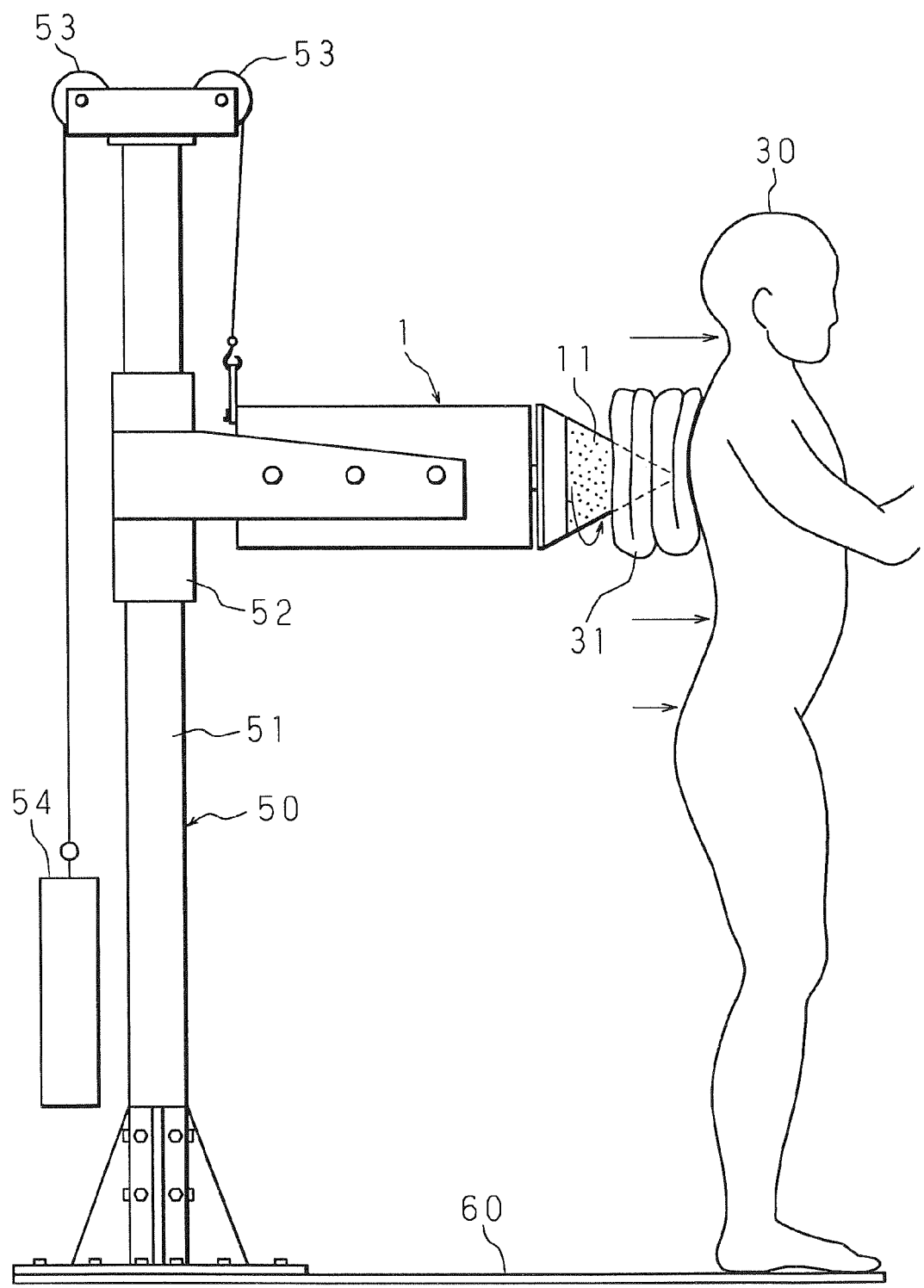
FIG. 10 is a side view showing a static electricity reducing/removing device according to the fifth embodiment of the present invention.

FIG. 10 is a side view showing a static electricity reducing/removing device according to the fifth embodiment of the present invention, in which 50 represents the static electricity reducing/removing device.

A stand 51 is mounted on one end of a static electricity reducing/removing board 60 of the static electricity reducing/removing device 50. A supporting unit 52 for supporting the static electricity reducing/removing instrument 1 is attached to the stand 51 so that it can be freely elevated and lowered, and pulleys 53 are attached to the upper section of the stand 51. The static electricity reducing/removing instrument 1 is supported by the supporting unit 52 in such a state that its end is hung up by one of the pulleys 53 and it is positioned in a horizontal direction by a weight 54 hung down from the other pulley 53.

Figure 11:
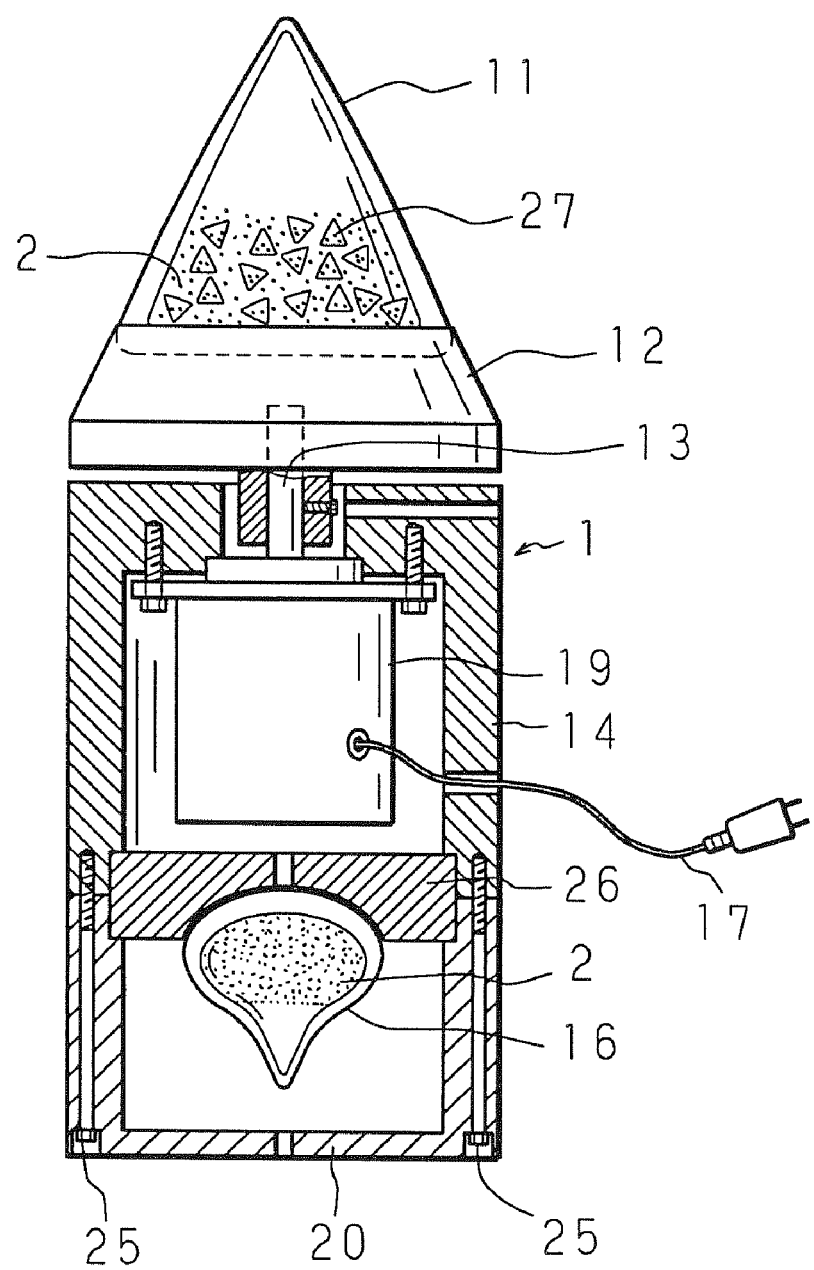
FIG. 11 is a cross sectional view showing a static electricity reducing/removing instrument applied to the fifth embodiment of the present invention.

FIG. 11 is a cross sectional view showing the static electricity reducing/removing instrument 1, in which the same parts as those shown in FIGS. 1 and 2 are designated with the same codes.

Stored in the motor storing unit 14 of this static electricity reducing/removing instrument 1 is the motor 19 (5IK150A-BF available from Oriental Motor Co. Ltd.: AC 100 V, 150 W output, 4.6 kg/cm torque, 3200 rpm rated speed).

The first glass container 11 has a base with a diameter of 120 mm and a height of 120 mm; and 0.6 kg of metallic silicon 2 and approximately 30 micro glass containers 27 (3 mm in diameter, 3 mm in height) in which the metallic silicon 2 is sealed are sealed in the first glass container 11. The second glass container 16 has a base with a diameter of 100 mm and a height of 100 mm.

It has been confirmed for the static electricity reducing/removing instrument 1 comprising the first glass container 11 in which 0.6 kg of metallic silicon 2 is sealed; and the static electricity reducing/removing instrument 1 of the fifth embodiment comprising the first glass container 11 in which 0.6 kg of metallic silicon 2 and approximately 30 micro glass containers 27 are sealed that the former tool has an effect on light symptoms such as stiff shoulders and lumbago and the latter tool also has an effect on heavy symptoms when they are brought into contact with human bodies while rotating the first glass container 11.

The static electricity reducing/removing instrument 1 is 450 mm in the entire length including the first glass container 11, 180 mm in diameter, and 27 kg in weight.

In the case when this static electricity reducing/removing device 50 is used, first, let a subject 30 stand on the other end of the static electricity reducing/removing board 60. Then, the supporting unit 52 is elevated or lowered according to the press position of the subject 30 and, after interposing a towel 31 between the pointed end of the first glass container 11 and the subject 30, the body of the subject 30 is pressed while rotating the first glass container 11.

(Case 1)

A female in her forties was unable to move suddenly because of a sudden slipped disk, but she recovered completely by receiving a treatment for reducing/removing static electricity using the static electricity reducing/removing device 50 of this fifth embodiment for 6 hours per day repeatedly for 5 days.

(Case 2)

A female in her seventies had symptoms of sensory paralysis in the whole right leg, lack of tactile sense, and reduced mobility and pain in the right shoulder joint, numbness and stiffness in the right and left hands, and arthralgia in the right and left elbows due to three traffic accidents and continued to have acupressure treatments, but she could not recover from these symptoms. When a treatment for reducing/removing static electricity was applied for 10 hours using the static electricity reducing/removing device 50 of the fifth embodiment, she recovered completely from these symptoms.

Sixth Embodiment

Figure 12:
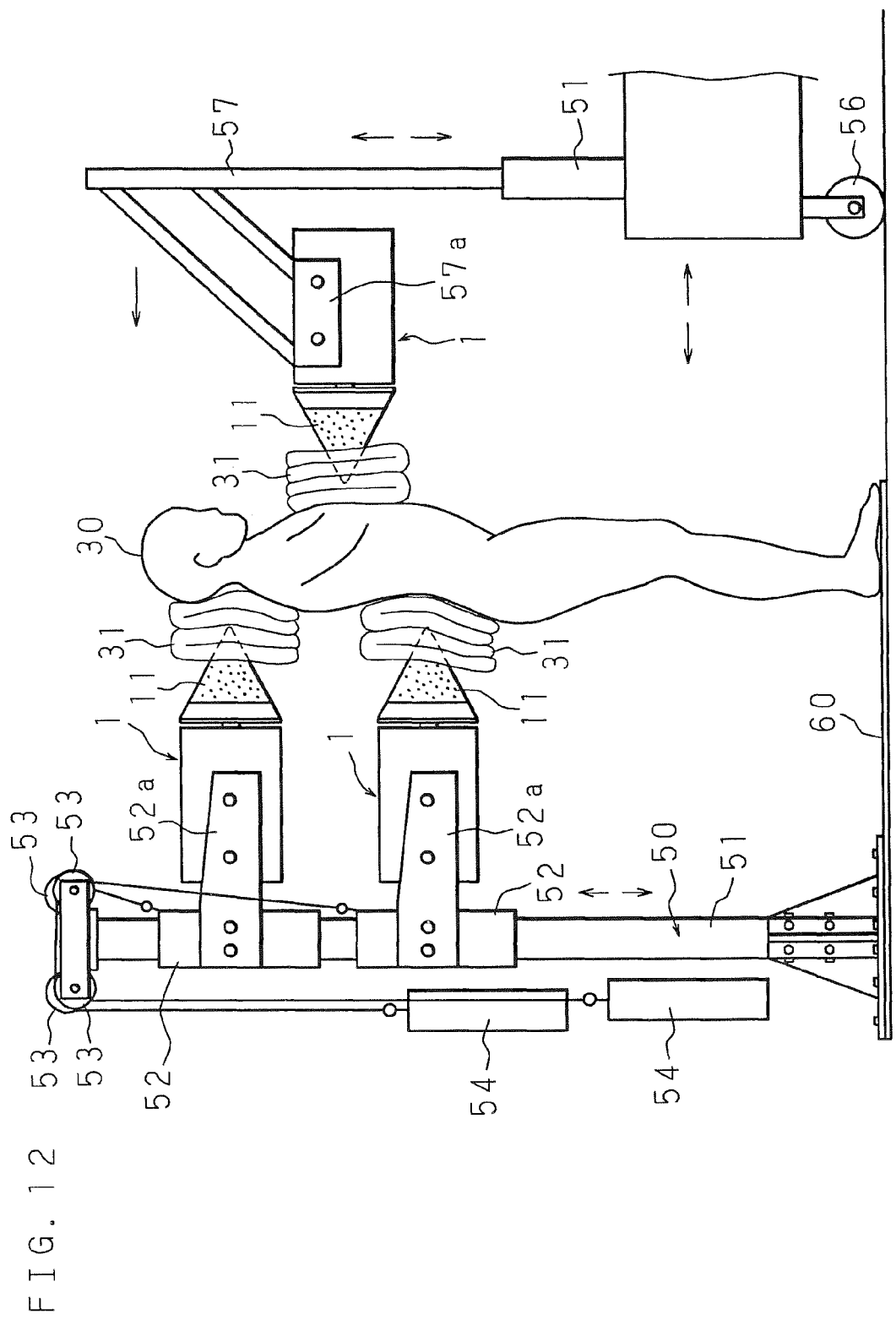
FIG. 12 is a side view showing a static electricity reducing/removing device according to the sixth embodiment of the present invention.

FIG. 12 is a side view showing a static electricity reducing/removing device according to the sixth embodiment, in which the same parts as those shown in FIG. 10 are designated with the same codes.

Supporting units 52 for supporting the static electricity reducing/removing instruments 1, respectively, are attached to one of the stands 51 mounted on the static electricity reducing/removing board 60 of the static electricity reducing/removing device 50 so that they can be freely elevated and lowered, and pulleys 53 are attached to the upper section of the stand 51. Each static electricity reducing/removing instrument 1 is supported by the supporting unit 52 in such a state that its end is hung up by one pulley 53 and it is positioned in a horizontal direction by a weight 54 hung down from the other pulley 53.

The other stand 51 has wheel parts 56 and is arranged so that it can move forward and backward along a direction approaching the subject 30. A supporting unit 57 for supporting a static electricity reducing/removing instrument 1 through a side part 57a is attached to this stand 51 so that it can be freely elevated and lowered.

Each of the static electricity reducing/removing instruments 1 of the static electricity reducing/removing device 50 is the same as the static electricity reducing/removing instrument 1 of the fifth embodiment shown in FIG. 11.

In this sixth embodiment, since one position on the front side of the subject 30 and two positions on the back side of the subject 30 are pressed simultaneously, it is effective to reduce/remove the static electricity in the deep part of the human body.

Next, the following description will explain specific cases where the static electricity reducing/removing device 50 according to the sixth embodiment was used for human bodies, and the effects of using the static electricity reducing/removing device 50.

(Case 1)

A female in her seventies had difficulty in taking care of her five-year old grandchild because of an extreme lowering of physical fitness, but she felt as if she became about 20 years younger after having a 12-hour static electricity reducing/removing treatment twice, and became able to do farm work and look after the grandchild vigorously.

(Case 2)

A female in her seventies has a symptom of cardiac infarction and had been in such a condition that she falls in a faint if she is slightly strained or has stress, for more than 30 years, but she has not yet had a cardiac infarction attack and shoulder stiffness after having a 12-hour static electricity reducing/removing treatment twice. She has no problem in looking after and bringing up her 11-year old grandchild.

(Case 3)

A male in his twenties had his neck sprained because he was fanned by strong wind when he unloaded a veneer from a track while carrying the veneer on his head during work. Although he went to a hospital regularly for more than 1 year, he could not recover from the strained neck and had stronger pain, and he lost his job. When he had a 6-hour static electricity reducing/removing treatment, he recovered completely from the strained neck and also from chronic gastritis.

Seventh Embodiment

Figure 13:
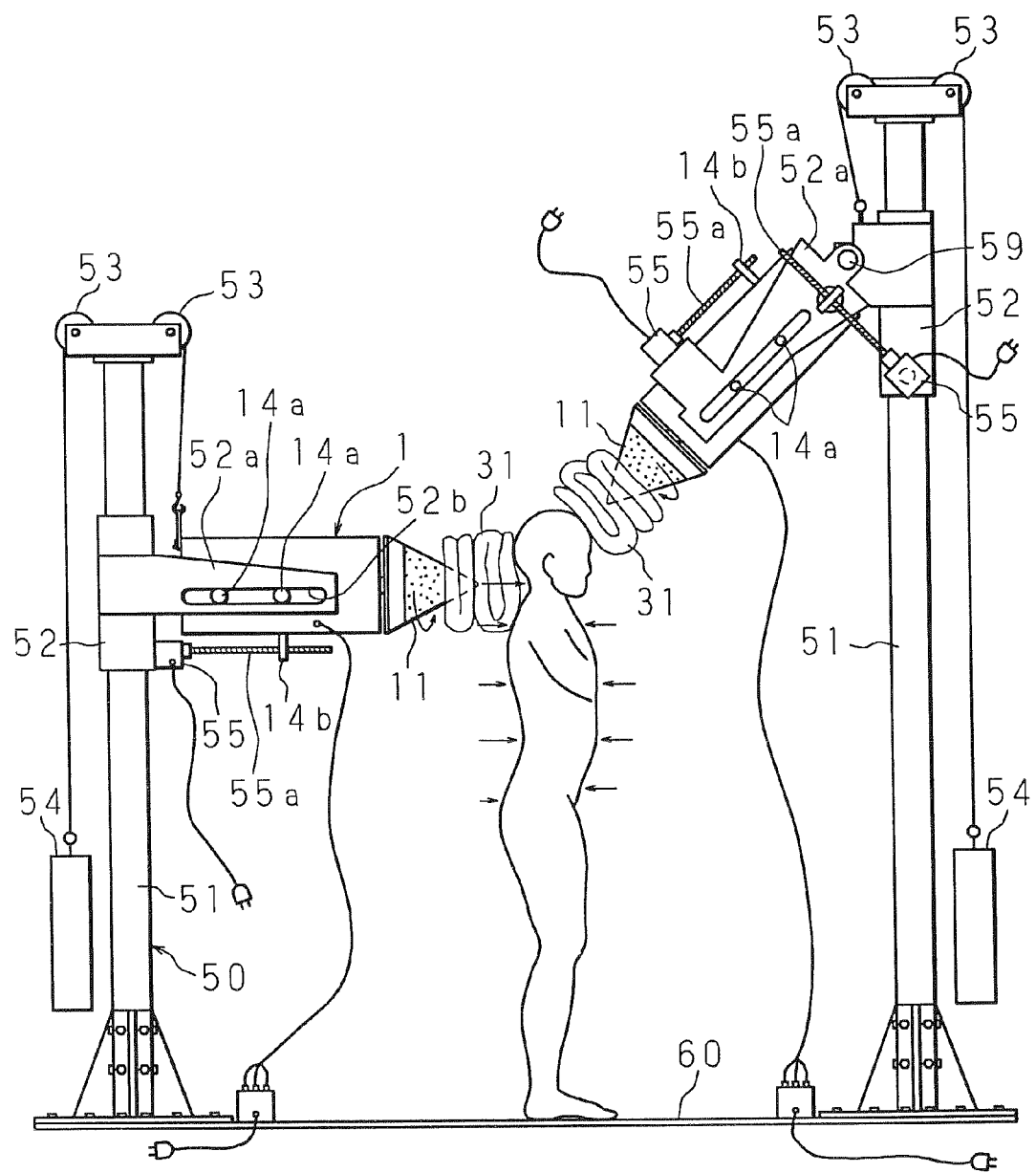
FIG. 13 is a side view showing a static electricity reducing/removing device according to the seventh embodiment of the present invention.

FIG. 13 is a side view showing a static electricity reducing/removing device according to the seventh embodiment of the present invention, in which the same parts as those shown in FIG. 10 are designated with the same codes.

In this seventh embodiment, the stands 51 are mounted on both ends of the static electricity reducing/removing board 60, and the subject 30 is arranged to stand the center position.

Provided on a side part 52a of the supporting unit 52 of one of the stands 51 is a guide part 52b for guiding pins 14a which are attached to the side face of the motor storing unit 14 of the static electricity reducing/removing instrument 1, in a horizontal direction. A static electricity reducing/removing instrument slide unit 55 (driving motor: VHR-560AM-GVH available from Oriental Motor Co. Ltd.) is attached to a lower section of the supporting unit 52, and, when a bolt part 55a of this static electricity reducing/removing instrument slide unit 55 is turned, a nut part 14b attached to the side face of the motor storing unit 14 slides and the pins 14a slide within the guide part 52a so as to move the static electricity reducing/removing instrument 1 forward and backward.

The static electricity reducing/removing instrument 1 is attached to the other stand 51 so that it can be moved forward and backward along a direction approaching a human body by the static electricity reducing/removing instrument slide unit 55 mounted on an end section of the side part 52a of the supporting unit 52 and is turned about a supporting point 59 between a horizontal direction and a direction of 45 degrees downward by a static electricity reducing/removing instrument inclination adjusting part 55 attached to a lower section of the supporting unit 52.

The static electricity reducing/removing instrument 1 of the static electricity reducing/removing device 50 have the same structure as the static electricity reducing/removing instrument 1 of the fifth embodiment shown in FIG. 11. The sizes of the first glass container 11 and second glass container 16 and the type of the motor 19 differ from those of the fifth and sixth embodiments.

The first glass container 11 has a base with a diameter of 180 mm and a height of 180 mm, and contains 1.2 kg of metallic silicon 2 and approximately 1000 micro glass containers 27 (3 mm in diameter, 3 mm in height). The size of the second glass container 16 is 180 mm in the diameter of the base and 180 mm in height.

The motor 19 is the three-phase AC motor VTFO-K2P available from Hitachi, Ltd., which has AC 200 V, 400 W output and 3200 rpm rated speed.

The static electricity reducing/removing instrument 1 is 720 mm in the entire length including the first glass container 11, 240 mm in diameter, and 55 kg in weight.

In this seventh embodiment, the supporting unit 52 of each static electricity reducing/removing device 50 is elevated or lowered according to the press position of the subject 30. Moreover, by moving the static electricity reducing/removing instrument 1 by the static electricity reducing/removing instrument slide part 55, the way of pressing is adjusted.

Next, the following description will explain the static electricity reducing/removing procedure according to the seventh embodiment.

(1) For reduction/removal of static electricity, a towel 31 is made substantially 20 cm in thickness and interposed between the static electricity reducing/removing instrument 1 and the subject 30, and the first glass container 11 is rotated.

(2) The static electricity reducing/removing instrument 1 is pressed against the body of the subject 30 suitably (to such an extent that the motor 19 is not overloaded), and kept in this state.

(3) If the pressed portion or periphery thereof has pathological disorder, the towel 31 is burnt black in two to three minutes and gives out smoke. If the subject 30 feels warm in the pressed portion in around five minutes, the static electricity reducing/removing instrument 1 is separated from the body and the towel 31 is exchanged.

(4) The steps of (1) to (3) are repeated for 20 minutes to complete one treatment.

(5) The steps of (1) to (4) are repeated for a different pressed portion.

Reduction/removal of static electricity is performed for the following pressed portions.

Figure 14:
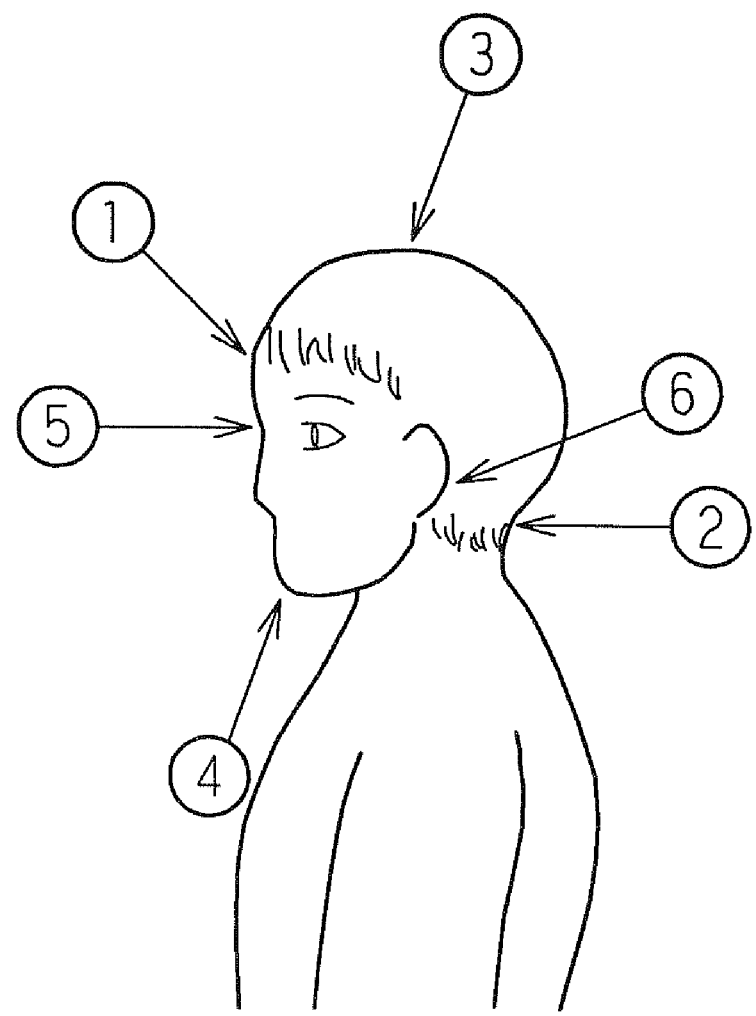
FIG. 14 is a side view showing portions of the head from which static electricity is reduced/removed.
Figure 15:
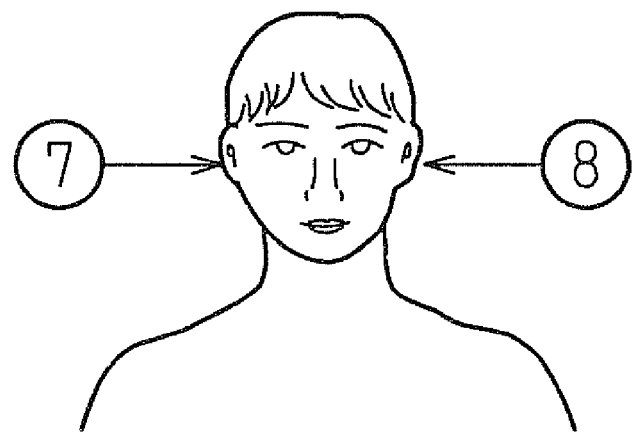
FIG. 15 is a front view showing portions of the ears from which static electricity is reduced/removed.

FIG. 14 is a side view showing portions of the head from which static electricity is reduced/removed; and FIG. 15 is a front view showing portions of the ears from which static electricity is reduced/removed.

The static electricity on the head is reduced/removed as follows.

(1) Reduction/removal of static electricity is performed for a hair boarder (1) and a recess (2) simultaneously.

(2) The static electricity on the top (3) of the head and a lower portion (4) of the maxillary is reduced/removed.

(3) The static electricity on a lower portion (5) between the eyes and the occiput portion (6) right behind the lower portion (5) is reduced/removed.

(4) The static electricity on lower portions (7) and (8) of both the ears is reduced/removed.

Figure 16:
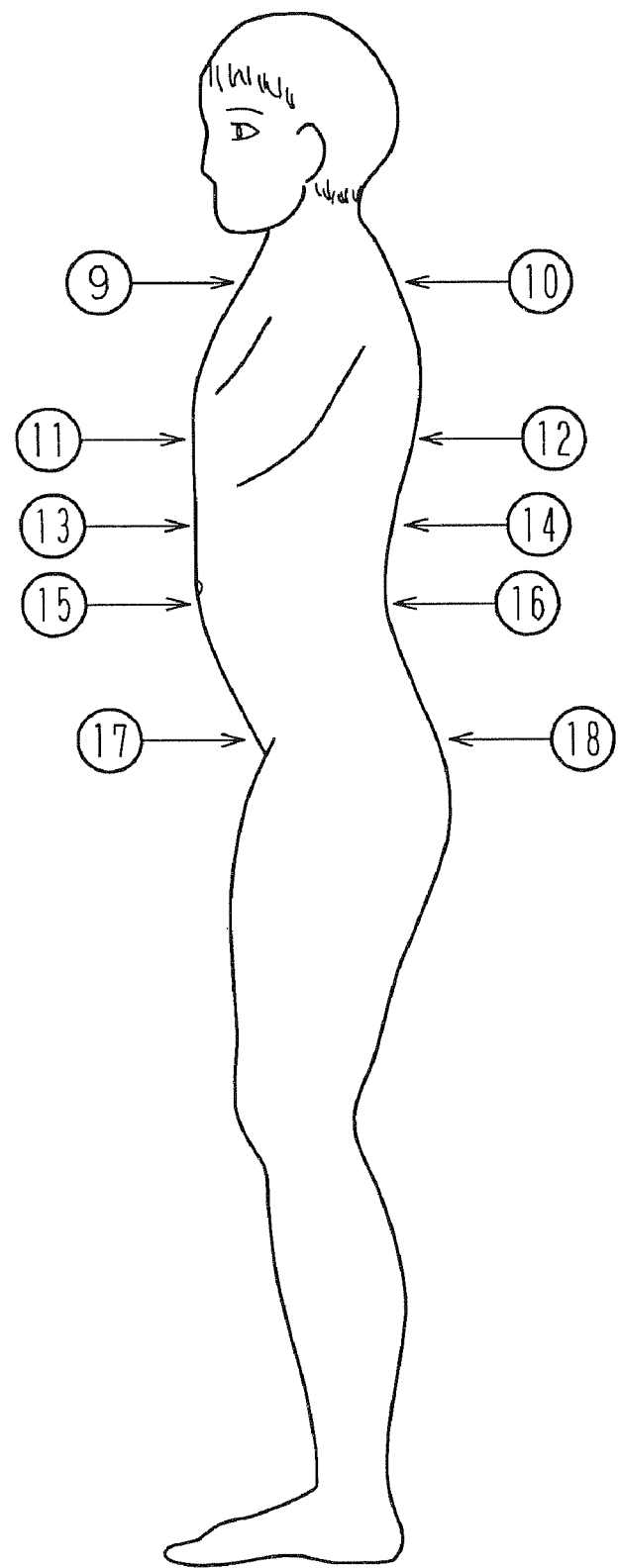
FIG. 16 is a side view showing portions of the trunk from which static electricity is reduced/removed.

FIG. 16 is a side view showing portions of the trunk from which static electricity is reduced/removed.

The static electricity on the trunk is reduced/removed as follows.

(1) Reduction/removal of static electricity is performed for an upper portion (9) of the joint of collarbones and an upper portion (10) of the most protruding part on the back side of the neck and backbone simultaneously.

(2) The static electricity on the pit (11) of the stomach and a backbone (12) right behind the pit (11) is reduced/removed.

(3) The static electricity on a portion (13) corresponding to the stomach just below the pit of the stomach and on a backbone (14) right behind the portion (13) is reduced/removed.

(4) The static electricity on a portion (15) 1 cm under the navel and on a backbone (16) right behind the portion (15) is reduced/removed.

(5) The static electricity on a pubis (17) and a backbone (18) right behind the pubis (17) is reduced/removed.

Figure 17:
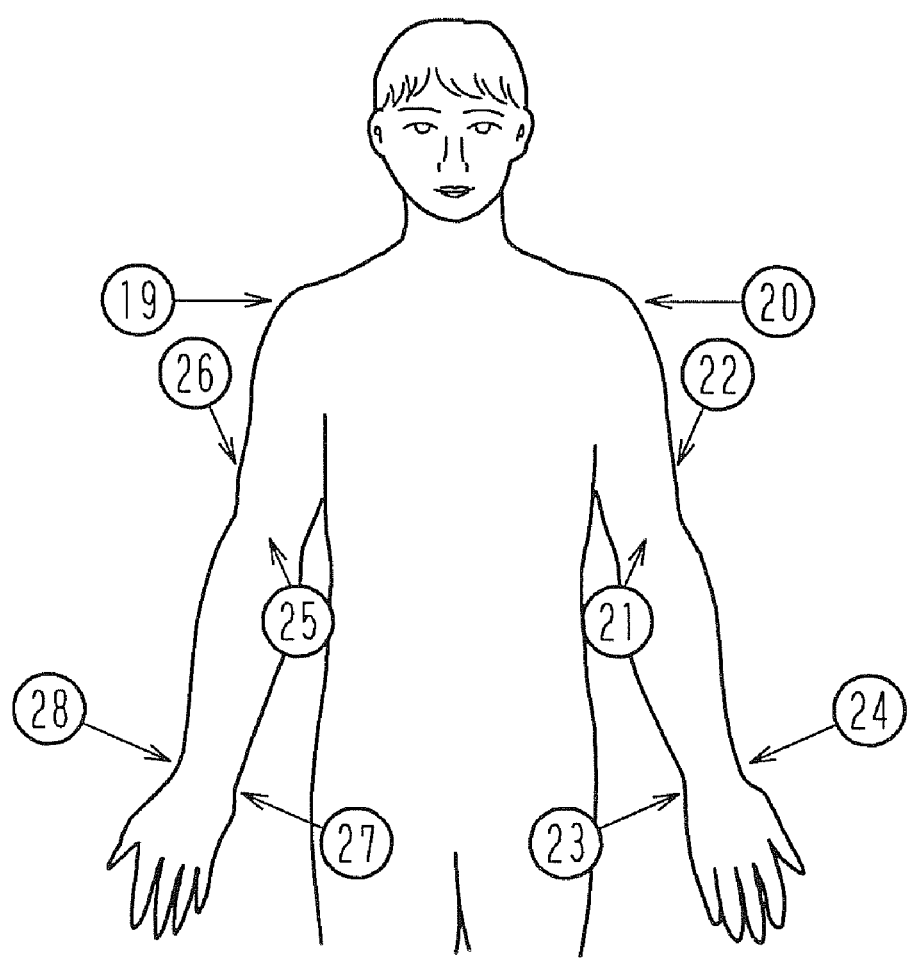
FIG. 17 is a front view showing portions of the shoulders and arms from which static electricity is reduced/removed.

FIG. 17 is a front view showing portions of the shoulders and arms from which static electricity is reduced/removed.

The static electricity on the shoulders and arms is reduced/removed as follows.

(1) Reduction/removal of static electricity is performed for lower portions (19) and (20) of both the shoulder bones simultaneously.

(2) The static electricity on an inner side (21) of an elbow joint and a portion (22) just above the left elbow bone is reduced/removed.

(3) The static electricity on a portion (23) between the wristbone at the joint of the left wrist and the palm and a portion (24) on the thumb side of the joint of the left wrist is reduced/removed.

(4) The static electricity on an inner side (25) of an elbow joint and a portion (26) just above the right elbow bone is reduced/removed.

(5) The static electricity on a portion (27) between the wristbone at the joint of the right wrist and the palm and a portion (28) on the thumb side of the joint of the left wrist is reduced/removed.

Regarding the legs, for each leg, reduction/removal of the static electricity is performed for the front and back sides of the knee joint simultaneously.

When a male in his forties had a static electricity reducing/removing treatment according to the above-described procedure, the electrostatic potential of each section of his body was measured before and after the static electricity reducing/removing treatment, and the results are shown in Table 4 below.

TABLE 4

|  | Top of head | Right shoulder | Base of right leg | Back side of right knee joint | Right knee joint | Front side of lumbar | Back side of lumbar |
|---|---|---|---|---|---|---|---|
| Before | 0.7 | 0.5 | 0.5 | 0.2 | 0.2 | 0.3 | 0.3 |
| After | 0.0 | 0.1 | 0.0 | −0.0 | 0.0 | 0.0 | 0.0 |

(unit: kV)

It will be understood from Table 4 that the electrostatic potential of each portion of the human body became smaller by reducing/removing static electricity.

Next, the following description will explain specific cases where the static electricity reducing/removing device 50 according to this seventh embodiment was used for human bodies, and the effects of using the static electricity reducing/removing device 50.

(Case 1)

A female in her thirties had a symptom that she had a feeling of uneasiness and was unable to smoothly talk with others, but she had no feeling of uneasiness and was able to talk to others after having a 6-hour static electricity reducing/removing treatment.

(Case 2)

A male in his fifties had symptoms of short breath, lowered physical fitness, inflexible body, and pain in the joints, but, after having a 24-hour static electricity reducing/removing treatment, he obtained a good physical condition and became able to reach the floor with his both palms when he bent forward.

(Case 3)

A male who was a dancer and in his forties had symptoms that he could not stretch his arms and legs satisfactorily in dancing and lost the sense of speed and accent in body movement, but he became able to move like he did in his twenties after having a treatment for a period of time.

(Case 4)

A male in his forties had symptoms of feeling heavy in his head and sleeplessness, but he felt light in the head and became able to sleep well after having a static electricity reducing/removing treatment.

(Case 5)

A female in her fifties had the visual acuity of 0.08 for the right eye and 0.09 for the left eye, and the refraction (equivalent spherical value) measured by an auto refractometer after mydriasis was −4.75 D for the right eye and −3.38 D for the left eye. Reduction/removal of static electricity was performed once a day for a total of six hours for 36 points of the body, such as the head, trunk and limbs, in such a manner that the static electricity reducing/removing treatment was applied to two points simultaneously, and, after repeating this treatment for three days, the visual acuity was measured 0.15 for the right eye and 0.6 for the let eye and the refraction (equivalent spherical value) measured by the auto refractometer after mydriasis was −3.5 D for the right eye and −2.13 D for the left eye. Considerable changes were not recognized between the results of general ophthalmologic inspections and blood and urine inspections performed before and after the static electricity reducing/removing treatment.

(Case 6)

For each of ten healthy persons having no systemic diseases and ophthalmologic diseases excluding defective sight, a total of 6-hour static electricity reducing/removing treatment for reducing/removing static electricity from 36 points of the body, such as the head, trunk and limbs, in such a manner that the static electricity on two points is simultaneously reduced/removed was repeated twice, and general ophthalmologic inspections including an inspection of ocular tension; blood and urine inspections; and measurement of blood pressure were performed. With reference to the ocular tension before the static electricity reducing/removing treatment, a significant lowering was recognized in the ocular tension until one week after applying the static electricity reducing/removing treatment twice. The ocular tensions (mean±SD) measured before the static electricity reducing/removing treatment, one day and one week after applying the static electricity reducing/removing treatment twice were 14.2±2.7 mmHg, 11.8±3.2 mmHg, 12.3±3.6 mmHg, respectively. Side effects considered as problems clinically were not recognized in terms of either the eyes or the whole body. Accordingly, it is considered that this treatment is an effective treatment for glaucoma.

(Case 7)

A male in his thirties suffered from severe diabetes, had the whole body swollen, felt a chill, and had lowered physical fitness and a blood glucose value of 490. After he had a 12-hour static electricity reducing/removing treatment, the swelling was subsided; and after he had a 60 hour static electricity reducing/removing treatment further, the blood glucose value was decreased to 230.

As described above, it was confirmed that the symptoms could be relieved by the use of the static electricity reducing/removing instrument 1 and static electricity reducing/removing device 50 according to the present invention.

Note that, while the respective embodiments illustrate examples where Si or $SiO_x$ is negatively charged and sealed in the first glass container 11 and the second glass container 16, the present invention is not limited to these examples, and it is possible to seal negatively charged mineral, Al, P, Ge, Sn, Pb, Ni, Fe, or the like in the first glass container 11 and the second glass container 16.

INDUSTRIAL APPLICABILITY

As described above, according to the first invention, by pressing the pointed section of the first glass container against an affected part, the blood flow in muscles can be improved sufficiently, and particularly when a plurality of the first glass containers are included, static electricity can be reduced/removed efficiently.

According to the second invention, the first glass container in which negatively charged Si or the like is sealed is included, and negative charges are emitted from the pointed section of this first glass container. By using this static electricity reducing/removing instrument, negative charges are efficiently supplied to a human body, and consequently symptoms such as muscular pain are alleviated.

According to the third invention, since the first glass container has a substantially conical shape, the directivity of negative charge emission is improved.

According to the fourth invention, since the driver for rotating or vibrating the first glass container is included and the first glass container is rotated or vibrated during application, a larger amount of negative charges are emitted, the immediate effect of removing static electricity from a subject of static electricity removal becomes higher, and static electricity in deep part can be removed. Accordingly, when this electrostatic reducing/removing tool comes into contact with the affected part of the human body, the flow of body fluids is further facilitated, thereby alleviating the symptoms.

According to the fifth invention, since the first glass container comprises a plurality of micro glass containers, the efficiently of emitting negative charges is improved, thereby limiting formation of blisters which were formed on the skin during reduction and removal of static electricity.

According to the sixth invention, since the second glass container having a pointed section and negatively charged Si or $SiO_x$ sealed therein is provided at the end portion thereof, it is possible to shorten the press time to human body, realize a long life of the driver, and prevent breakdown of the first glass container and adhesion of iron dioxide as an impurity to the inner wall of the first glass container.

According to the seventh and eighth inventions, since Si or the like is placed in a stationary state at a location where static electricity reducing/removing means is buried, or Si or the like is introduced into a negatively charged quartz crucible, the Si or the like turns into a negatively charged state by migration of negative charges to the Si or the like, and the negative charges are fixed to the Si or the like by the following sintering process, thereby limiting a decrease of negative charges with time. When a static electricity reducing/removing instrument is constructed by sealing Si or the like negatively charged in this manner in the first glass container, negative charges are efficiently supplied during application.

According to the ninth and tenth invention, the static electricity reducing/removing instrument which is heavy in weight is fixed to the supporting base, and the pointed end of the first glass container can be brought into contact with an affected part accurately by fixing the static electricity reducing/removing instrument during rotation. Moreover, since reduction/removal of static electricity can be performed for the front and back sides of a human body simultaneously, negative charges are efficiently supplied to the human body, thereby enhancing the effects of relieving symptoms.

The invention claimed is:

1. A method for using a static electricity reducing/removing instrument for a body part located in an environment in which said instrument is also located, the instrument comprising, at an end portion thereof, at least one first glass container having a pointed section constructed to be pressed against the body part and Si (silicon), SiOx (a silicon oxide, where $0<x\leq2$), mineral, Al (aluminum), P (phosphorous), Ge (germanium), Sn (tin), Pb (lead), Ni (nickel) or Fe (iron) in granular or powder form sealed therein, said first glass container containing a plurality of micro glass containers in which negatively charged Si (silicon), SiOx (a silicon oxide, where $0<x\leq2$), mineral, Al (aluminum), P (phosphorous), Ge (germanium), Sn (tin), Pb (lead), Ni (nickel) or Fe (iron) in granular or powder form sealed is sealed, said method comprising the step of touching the pointed section to the body part.

2. The method of claim 1 performed with a first glass container which has a substantially conical shape.

3. The method of claim 1 performed with a first glass container contains a plurality of micro glass containers in which Si (silicon), SiOx (a silicon oxide, where $0<x\leq2$), mineral, Al (aluminum), P (phosphorous), Ge (germanium), Sn (tin), Pb (lead), Ni (nickel) or Fe (iron) in granular or powder form is sealed.

4. The method of claim 1, wherein prior to the touching step, the following steps are performed:
placing the granules or powder in a stationary state at a location where said method is to be performed by sealing Si (silicon) or SiOx (a silicon oxide, where $0<x\leq2$), in granular or powder form in a glass tube; and
sintering the granules or powder, at said location.

5. The method of claim 1, wherein the touching step is performed with means having at least one supporting base for elevating and lowering at least one container while said pointed section faces a human body, the base being constructed to press the pointed section against the body part.

6. The method of claim 1, wherein the touching step is performed with means having at least one supporting base for supporting at least one container while said pointed section is movable forward and backward along a direction approaching a human body, the base being constructed to press the pointed section against the body part.

7. The method of claim 1 wherein said Si (silicon), SiOx (a silicon oxide, where $0<x\leq2$) mineral, Al (aluminum), P (phosphorous), Ge (germanium), Sn (tin), Pb (lead), Ni (nickel) or Fe (iron) is negatively charged.

8. The method of claim 7 performed with a first glass container which has a substantially conical shape.

9. The method of claim 7 performed with a first glass container contains a plurality of micro glass containers in which negatively charged Si (silicon), SiOx (a silicon oxide, where $0<x\leq2$), mineral, Al (aluminum), P (phosphorous), Ge (germanium), Sn (tin), Pb (lead), Ni (nickel) or Fe (iron) in granular or powder form is sealed.

10. The method of claim 7, wherein prior to the touching step, the following steps are performed:
placing the granules or powder in a stationary state at a location where said method is to be performed by sealing it in a glass tube; and
sintering the granules or powder, at said location.

11. The method of claim 7, wherein prior to the touching step, the following steps are performed:
introducing the granules or powder in a negatively charged quartz crucible; and
sintering them in a glass tube.

12. The method of claim 7, wherein the touching step is performed with means having at least one supporting base for elevating and lowering at least one container while said pointed section faces a human body, the base being constructed to press the pointed section against the body part.

13. The method of claim 7, wherein the touching step is performed with means having at least one supporting base for supporting at least one container while said pointed section is movable forward and backward along a direction approaching a human body, the base being constructed to press the pointed section against the body part.

* * * * *